United States Patent
Schultz et al.

(10) Patent No.: US 11,078,419 B2
(45) Date of Patent: *Aug. 3, 2021

(54) SUBSTITUTED BENZOTRIAZOLE PHENOLATE SALTS AND ANTIOXIDANT COMPOSITIONS FORMED THEREFROM

(71) Applicant: 3M INNOVATIVE PROPERTIES COMPANY, St. Paul, MN (US)

(72) Inventors: Nathan E. Schultz, Woodbury, MN (US); Fuming B. Li, Woodbury, MN (US); Kelly A. Volp, Minneapolis, MN (US); Mark McCormick, St. Paul, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/780,323

(22) Filed: Feb. 3, 2020

(65) Prior Publication Data
US 2020/0172809 A1 Jun. 4, 2020

Related U.S. Application Data

(62) Division of application No. 15/741,680, filed as application No. PCT/US2016/040370 on Jun. 30, 2016, now Pat. No. 10,669,481.

(60) Provisional application No. 62/189,473, filed on Jul. 7, 2015.

(51) Int. Cl.
| | |
|---|---|
| *C09K 15/32* | (2006.01) |
| *C08K 5/00* | (2006.01) |
| *C09K 15/24* | (2006.01) |
| *C07D 249/20* | (2006.01) |
| *C08K 5/138* | (2006.01) |
| *C08K 5/3475* | (2006.01) |
| *C08L 23/12* | (2006.01) |
| *G01R 33/46* | (2006.01) |

(52) U.S. Cl.
CPC ............ *C09K 15/32* (2013.01); *C07D 249/20* (2013.01); *C08K 5/0091* (2013.01); *C08K 5/138* (2013.01); *C08K 5/3475* (2013.01); *C09K 15/24* (2013.01); *C08L 23/12* (2013.01); *C08L 2201/08* (2013.01); *G01R 33/46* (2013.01)

(58) Field of Classification Search
None
See application file for complete search history.

(56) References Cited

U.S. PATENT DOCUMENTS

| | | | |
|---|---|---|---|
| 30,782 | A | 11/1860 | Wright |
| 31,285 | A | 1/1861 | Miller |
| 32,171 | A | 4/1861 | Alexander |
| 3,971,373 | A | 7/1976 | Braun |
| 4,100,324 | A | 7/1978 | Anderson |
| 4,118,531 | A | 10/1978 | Hauser |
| 4,215,682 | A | 8/1980 | Kubik |
| 4,251,435 | A | 2/1981 | Son |
| 4,264,750 | A | 4/1981 | Anand |
| 4,340,563 | A | 7/1982 | Appel |
| 4,375,718 | A | 3/1983 | Wadsworth |
| 4,429,001 | A | 1/1984 | Kolpin |
| 4,508,781 | A | 4/1985 | Yagi |
| 4,557,945 | A | 12/1985 | Yagi |
| 4,588,537 | A | 5/1986 | Klaase |
| 4,592,815 | A | 6/1986 | Nakao |
| 4,652,282 | A | 3/1987 | Ohmori |
| 4,789,504 | A | 12/1988 | Ohmori |
| 4,874,659 | A | 10/1989 | Ando |
| 5,057,710 | A | 10/1991 | Nishiura |
| 5,096,977 | A | 3/1992 | MacLeay |
| 5,110,849 | A | 5/1992 | Karasawa |
| 5,233,047 | A | 8/1993 | MacLeay |
| 5,401,446 | A | 3/1995 | Tsai |
| 5,496,507 | A | 3/1996 | Angadjivand |
| 5,663,128 | A | 9/1997 | Evans |
| 5,871,845 | A | 2/1999 | Dahringer |
| 5,908,598 | A | 6/1999 | Rousseau |
| 5,914,186 | A | 6/1999 | Yau |
| 5,919,847 | A | 7/1999 | Rousseau |
| 5,922,882 | A | 7/1999 | Mori |
| 5,968,635 | A | 10/1999 | Rousseau |
| 5,976,208 | A | 11/1999 | Rousseau |
| 6,213,122 | B1 | 4/2001 | Rousseau |
| 6,214,094 | B1 | 4/2001 | Rousseau |
| 6,238,466 | B1 | 5/2001 | Rousseau |

(Continued)

FOREIGN PATENT DOCUMENTS

| | | |
|---|---|---|
| EP | 0351732 | 1/1990 |
| EP | 0447166 | 9/1991 |

(Continued)

OTHER PUBLICATIONS

Antalek, "Using pulsed gradient spin echo NMR for chemical mixture analysis: How to obtain optimum results", Concepts in Magnetic Resonance, 2002, vol. 14, No. 4, pp. 225-258.

(Continued)

*Primary Examiner* — Robert T Butcher
(74) *Attorney, Agent, or Firm* — Jeffrey M. Olofson

(57) ABSTRACT

A class of antioxidant compositions include benzotriazole phenolate salts with substituents either ortho to the phenol hydroxide group and/or para to the phenol hydroxide group can be prepared from substituted benzotriazole phenols. The ortho substituent group can be a simple hydrocarbon, alkoxy or amino group, or the ortho substituent group can be a linking group, linking the benzotriazole phenolate to another benzotriazole phenolate group.

16 Claims, 1 Drawing Sheet

(56) References Cited

U.S. PATENT DOCUMENTS

| | | | |
|---|---|---|---|
| 6,268,495 | B1 | 7/2001 | Rousseau |
| 6,365,088 | B1 | 4/2002 | Knight |
| 6,375,886 | B1 | 4/2002 | Angadjivand |
| 6,397,458 | B1 | 6/2002 | Jones |
| 6,398,847 | B1 | 6/2002 | Jones |
| 6,406,657 | B1 | 6/2002 | Eitzman |
| 6,409,806 | B1 | 6/2002 | Jones |
| 6,419,871 | B1 | 7/2002 | Ogale |
| 6,432,175 | B1 | 8/2002 | Jones |
| 6,451,887 | B1 | 9/2002 | Wood |
| 6,454,986 | B1 | 9/2002 | Eitzman |
| 6,524,488 | B1 | 2/2003 | Insley |
| 6,562,112 | B2 | 5/2003 | Jones |
| 6,607,624 | B2 | 8/2003 | Berrigan |
| 6,660,210 | B2 | 12/2003 | Jones |
| 6,743,464 | B1 | 6/2004 | Insley |
| 6,789,241 | B2 | 9/2004 | Anderson |
| 6,800,676 | B2 | 10/2004 | Wood |
| 6,808,551 | B2 | 10/2004 | Jones |
| 6,824,718 | B2 | 11/2004 | Eitzman |
| 6,916,752 | B2 | 7/2005 | Berrigan |
| 7,244,291 | B2 | 7/2007 | Spartz |
| 7,244,292 | B2 | 7/2007 | Kirk |
| 7,390,351 | B2 | 6/2008 | Leir |
| 7,765,698 | B2 | 8/2010 | Sebastian |
| 8,162,153 | B2 | 4/2012 | Fox |
| 8,790,449 | B2 | 7/2014 | Li |
| 2002/0174869 | A1 | 11/2002 | Gahan |
| 2003/0004235 | A1 | 1/2003 | Wood |
| 2003/0134515 | A1 | 7/2003 | David |
| 2003/0165711 | A1 | 9/2003 | Kim |
| 2003/0192231 | A1 | 10/2003 | Wood |
| 2003/0213164 | A1 | 11/2003 | Pastor |
| 2004/0092634 | A1 | 5/2004 | Arnoldi |
| 2008/0038976 | A1 | 2/2008 | Berrigan |
| 2011/0092620 | A1 | 4/2011 | Scheffner |
| 2012/0302760 | A1 | 11/2012 | Preschel |

FOREIGN PATENT DOCUMENTS

| | | |
|---|---|---|
| EP | 0623941 | 11/1994 |
| EP | 0644195 | 3/1995 |
| FR | 1324897 | 4/1963 |
| JP | 02292357 | 12/1990 |
| JP | 06254319 | 9/1994 |
| JP | 08284063 | 10/1996 |
| JP | H09-111234 | 4/1997 |
| JP | 2002212439 | 7/2002 |
| WO | WO 1993-14510 | 7/1993 |
| WO | WO 2001-07144 | 2/2001 |
| WO | WO 2002-14419 | 2/2002 |
| WO | WO 2002-098968 | 12/2002 |
| WO | WO 2008-131921 | 11/2008 |
| WO | WO 2009-076064 | 6/2009 |
| WO | WO 2009-148744 | 12/2009 |
| WO | WO 2009-148747 | 12/2009 |
| WO | WO 2010-114742 | 10/2010 |
| WO | WO 2011-005711 | 1/2011 |
| WO | WO 2011-137142 | 11/2011 |
| WO | WO 2012-163936 | 12/2012 |
| WO | WO 2014-105107 | 7/2014 |
| WO | WO 2014-172308 | 10/2014 |
| WO | WO 2017-007672 | 1/2017 |
| WO | WO 2017-007673 | 1/2017 |
| WO | WO 2017-007675 | 1/2017 |

OTHER PUBLICATIONS

Auge, "NMR Measure of Translational Diffusion and Fractal Dimension. Application to Molecular Mass Measurement", The Journal of Physical Chemistry B, 2009, vol. 113, No. 7, pp. 1914-1918.

Belusa, "2-(2-Hydroxyphenyl) benzotriazoles. I. Synthesis and their ultraviolet and infrared spectra", Chemicke Zvesti, 1974, vol. 28, No. 5, pp. 673-679.

Belusa, "2-(2-Hydroxyphenyl) benzotriazoles. II. Electrophilic substitution reactions on the molecule of 2-(2-hydroxy--5-methylphenyl) benzotriazole and ultraviolet spectra of the products", Chemicke Zvesti, Jan. 1974, vol. 28 No. 5, pp. 680-685.

Belusa, "Synthesis of 2,2-bis-/4-hydroxy-3,5-di-(2-benzotriazolyl) phenyl/propane", Tetrahedron Letters, 1968, vol. 9, No. 10, pp. 1167-1170.

Berliner, "Synthesis of Alpha-Halo Ethers from Symmetric Acetals and In Situ Methoxymethylation of an Alcohol", Organic Syntheses, 2007, vol. 84, pp. 102-110.

Burgos, "Significantly Improved Method for the Pd-Catalyzed Coupling of Phenols with Aryl Halides: Understanding Ligand Effects", Angewandte Chemie International Edition, Jun. 2006, vol. 45, No. 26, pp. 4321-4326.

Carofiglio, "UV stabilizers bonded to transition metals: Synthesis and X-ray structure of 2-(2'-hydroxphenyl)benzotriazole-oxovanadium(IV) and -d ioxomolybdenum(VI) complexes", Polyhedron, Sep. 1996, vol. 15, No. 24, pp. 4435-4440.

Cheung, "Palladium-Catalyzed Hydroxylation of Aryl and Heteroaryl Halides Enabled by the Use of a Palladacycle Precatalyst", The Journal of Organic Chemistry, Apr. 2012, vol. 79, No. 11, pp. 5351-5358.

Davies, "The Separation of Airborne Dust and Particles," Proceedings of the Institution of Mechanical Engineers, Part B: Journal of Engineering Manufacture, 1952, vol. 1B, pp. 185-198.

Dennis, "Procyanidin oligomers. A new method for 4→8 interflavan bond formation using C8-boronic acids and iterative oligomer synthesis through a boron-protection strategy", Tetrahedron, Jan. 2012, vol. 68, No. 1, pp. 340-348.

Evans, "Synthesis of diaryl ethers through the copper-promoted arylation of phenols with arylboronic acids. An expedient synthesis of thyroxine", Tetrahedron Letters, 1998, vol. 39, No. 19, pp. 2937-2940.

Kürti, Strategic Applications of Named Reactions in Organic Synthesis, 2005, pp. 464-465.

Li, "Synthesis and structural characterization of zinc complexes supported by amino-benzotriazoie phenoxide ligands: Efficient catalysts for ring-opening polymerization of ε-caprolactone and β-butyrolactone", Inorganic Chemistry Communications, 2011, vol. 14, No. 07, pp. 1140-1144, XP028220554.

Maliakal, "Twisted Intramolecular Charge Transfer States in 2-Arylbenzotriazoles: Fluorescence Deactivation via Intramolecular Electron Transfer Rather Than Proton Transfer", Journal of Physical Chemistry A, 2002, vol. 106, No. 34, pp. 7680-7689, XP055294802.

Matteucci, Mild and Highly Chemoselective Oxidation of Thioethers Mediated by Sc(OTf)$_3$, Organic Letters, 2003, vol. 5, No. 3, pp. 235-237.

Neufeld, "Accurate molecular weight determination of small molecules via DOSY-NMR by using external calibration curves with normalized diffusion coefficients", Chemical Science, 2015, vol. 6, pp. 3354-3364.

Nilsson, "The DOSY Toolbox: A new tool for processing PFG NMR diffusion data", Journal of Magnetic Resonance, 2009, vol. 200, No. 2, pp. 296-302.

Rosevear, "Preparation of some 2-(2' H-Benzotriazol-2'-yl)phenol ultraviolet absorbers: Application of the transalkylation reaction", Australian Journal of Chemistry, 1985, vol. 38, No. 08, pp. 1163-1176, XP055294724.

Seechurn, "Palladium-Catalyzed Cross-Coupling: A Historical Contextual Perspective to the 2010 Nobel Prize", Angewandte Chemie International Edition, May 2012, vol. 51, No. 21, pp. 5062-5085.

Valiev, "NWChem: a comprehensive and scalable open-source solution for large scale molecular simulations", Computer Physics Communications, 2010, vol. 181, No. 9, pp. 1477-1489.

Varma, "The Urea-Hydrogen Peroxide Complex: Solid-State Oxidativve Protocols for Hydroxylated Adehydes and Ketones (Dakin Reaction), Nitriles, Sulfides, and Nitrogen Heterocycles", Organic Letters,1991, vol. 1, No. 2, pp. 189-191.

Waker, "Application of Cavity Theory to the Discharge of Electrostatic Dust Filters by x-Rays", International Journal of Radiation

(56) References Cited

OTHER PUBLICATIONS

Applications and Instrumentation. Part A. Applied Radiation and Isotopes, 1988, vol. 39, No. 7, pp. 677-684.
Wente, "Superfine Thermoplastic Fibers," Industrial and Engineering Chemistry, Aug. 1956, vol. 48, No. 8, pp. 1342-1346.
Wente, "Manufacture of Superfine Organic Fibers", Report No. 4364 of the Naval Research Laboratories, May 1954, pp. 1-20.
Wu, "A Single Phosphine Ligand Allows Palladium-Catalyzed Intermolecular CO Bond Formation with Secondary and Primary Alcohols", Angewandte Chemie International Edition, Sep. 2011, vol. 50, No. 42, pp. 9943-9947.
Xu, "Synthesis of diaryl-azo derivatives as potential antifungal agents", Bioorganic & Medicinal Chemistry Letter, Jul. 2010, vol. 20, No. 14, pp. 4193-4195.
International Search Report for PCT International Application No. PCT/US2016/040370, dated Sep. 16, 2016, 5 pages.
Machine Translation of JP H09-111234, Enokida et al, Apr. 1997, p. 1-7.

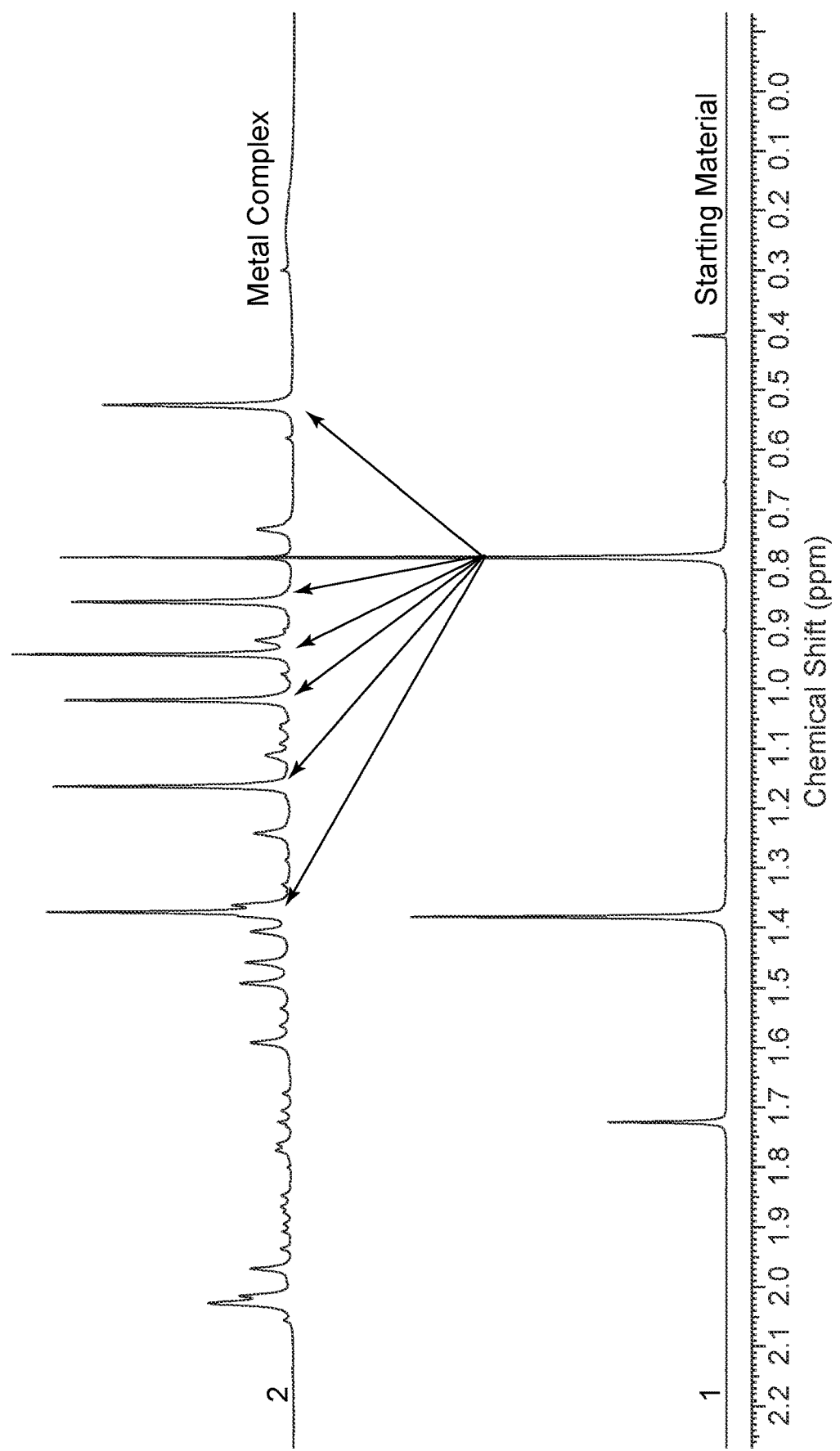

SUBSTITUTED BENZOTRIAZOLE PHENOLATE SALTS AND ANTIOXIDANT COMPOSITIONS FORMED THEREFROM

FIELD OF THE DISCLOSURE

This disclosure relates to substituted benzotriazole phenolate salts and antioxidant compositions formed from them.

BACKGROUND

Phenols are a class of chemical compounds having a hydroxyl group directly bonded to an aromatic hydrocarbon group. Phenolates are the anionic salts of phenols in which a proton has been removed from the hydroxyl group of the phenol. A wide variety of phenolics, as compounds that contain a phenol group are called, are known. Some phenolics are produced by plants in nature and others have been synthetically designed for a variety of chemical uses.

One class of phenolics are 2-(2-hydroxyphenyl)benzotriazoles or benzotriazole phenols. Benzotriazole phenols are an important class of UV absorbers, and in some cases, can absorb in the visible range as well. These compounds are often used as additives in materials and can even be incorporated into the polymeric structures via a polymerizable substituent on the benzotriazole phenol structure.

In addition to the usefulness of the benzotriazole phenols themselves, the benzotriazole phenols can also be used as synthons to form benzotriazole phenolate salts that are also useful. For example in EP Patent Publication No. 351,732, the use of a variety of benzotriazole phenolate salts are used as the essential ingredient to give high crystallization rates in polyester polymer compositions.

The need remains for substituted benzotriazole phenolate salts.

SUMMARY

Disclosed herein are substituted benzotriazole phenolate salts, and antioxidant compositions comprising these substituted benzotriazole phenolate salts. In some embodiments, the antioxidant composition comprises one or more macromolecular salt compositions, the macromolecular salt composition comprising an assembly of metal salts comprising repeat units of a substituted benzotriazole phenolate anion and a metal cation with the structure:

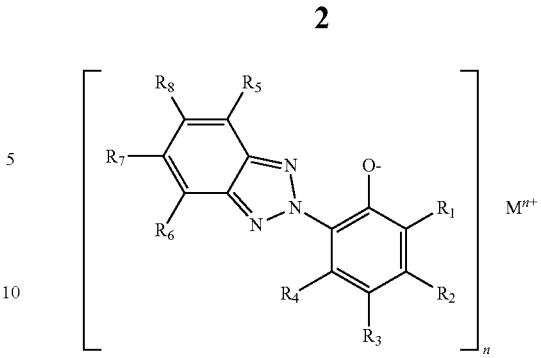

where each $R^1$, $R^2$, $R^3$, $R^4$, $R^5$, $R^6$, $R^7$, and $R^8$, independently comprises a hydrogen atom, an alkyl group, an alkenyl group, an aryl group, a halogen atom, or a substituted heteroatom group comprising a —B(OR$^{18}$)(OR$^{19}$), a —SiR$^{20}{}_3$, a —CH$_2$—R$^9$, an —O—R$^9$, a —N—R$^9$R$^{10}$, a —S—R$^9$, a —S(O)—R$^9$, or a —S(O)$_2$—R$^9$ group, where S(O) is a sulfinyl group S═O, and S(O)$_2$ is a sulfonyl group O═S═O, R$^9$ comprises a hydrogen atom, an alkyl group, an alkenyl group, an aryl group, or a heteroatom-containing group comprising one or more oxygen, nitrogen, sulfur, or phosphorous atoms, wherein the —B(OR$^{18}$)(OR$^{19}$), —SiR$^{20}{}_3$, —CH$_2$—R$^9$, —O—R$^9$, —N—R$^9$R$^{10}$, —S—R$^9$, —S(O)—R$^9$, or —S(O)$_2$—R$^9$ group may be neutral or anionic, and R$^{10}$ comprises a hydrogen atom, an alkyl group, an alkenyl group, an aryl group, or a heteroatom-containing group comprising one or more oxygen, nitrogen, sulfur, or phosphorous atoms, or R$^9$ and R$^{10}$ together with the atoms connecting form a heterocyclic ring structure, R$^{18}$ and R$^{19}$ are independently hydrogen atoms, alkyl groups or R$^8$ and R$^{19}$ together with the atoms connecting form a heterocyclic ring structure, each R$^{20}$ independently comprises an alkyl group; n is an integer of 1-4; and M comprises a metal atom with a valency of n; and the macromolecular assembly comprises 2-4 repeat units.

In other embodiments, the repeat unit of the macromolecular salt has the structure:

where X comprises a —CH$_2$—, —O—, —S—, —S(O)—, —S(O)$_2$—, or —NR$^{10}$— linking group where R$^{10}$ comprises a hydrogen atom, an alkyl group, or an aryl group, each R$^2$, R$^3$, R$^4$, R$^5$, R$^6$, R$^7$, R$^8$, R$^{11}$, R$^{12}$, R$^{13}$, R$^{14}$, R$^{15}$, R$^{16}$, and R$^{17}$, independently comprises a hydrogen atom, an alkyl group, an alkenyl group, an aryl group, or a halogen atom; m=0.5, 1, or 2; M is a metal ion with a valency of 2m such that M is lithium sodium or potassium when m=0.5; M is calcium, magnesium, or cobalt, when m=1; and M is vanadium or titanium when m=2.

BRIEF DESCRIPTION OF THE DRAWINGS

The present application may be more completely understood in consideration of the following detailed description of various embodiments of the disclosure in connection with the accompanying drawings.

The FIGURE shows a view of NMR data for a precursor and for an embodiment of an article of this disclosure.

DETAILED DESCRIPTION

One class of useful phenolics are 2-(2-hydroxyphenyl) benzotriazoles or benzotriazole phenols. Benzotriazole phenols are an important class of UV absorbers, and in some cases, can absorb in the visible range as well. These compounds are often used as additives in materials, particularly polymeric materials, and can be used as synthons to prepare benzotriazole phenolate salts, which can also be useful as additives in materials, especially polymeric materials.

Phenols such as benzotriazole phenols are known to be absorbers of light, especially UV (ultraviolet) light, but also in some instances visible light. A number of benzotriazole phenols are commercially available as light stabilizers, that is to say for incorporation into polymeric matrices to protect the matrices from damage by UV light.

Disclosed herein are substituted benzotriazole phenolate salts which have a wide variety of desirable properties. The substituted benzotriazole phenolate salts have antioxidant properties. That is to say that incorporation of the phenolate salts into polymeric matrices protects that matrices from oxidation. This is very different from the light stabilization properties of the phenols. This antioxidant property can be measured in a variety of ways as will be described in greater detail in the Examples section below. The ability of these salts to provide protection from oxidation is a very useful property, as well as one that is not expected for this class of materials.

In addition, the substituted benzotriazole phenolate salts also have the unexpected property of fluorescence. Fluorescence is a well understood property in which the material absorbs electromagnetic radiation of one wavelength and emits electromagnetic radiation of different, typically longer, wavelength. In the present disclosure, the substituted benzotriazole phenolate salts absorb light of UV wavelengths and emits light in the visible range of wavelengths. This property has a wide range of uses, particularly when the fluorescent material is dispersed within a polymeric matrix. For example, a wide variety of safety and security items utilize this property from signs and other safety articles where the fluorescence enhances the visibility of the safety articles, to security articles which can use the fluorescence for verification (the presence of fluorescence in a security document allows for verification of the authenticity of the security document by exposure to UV light and observation of the fluorescence). The fluorescence of the substituted benzotriazole phenolate salts is surprising in view of the fact that the phenols from which the salts are prepared are not fluorescent.

Another property of these substituted benzotriazole phenolate salts is their usefulness as charge enhancing additives for electret materials. This property is more fully disclosed in U.S. Ser. No. 62/189,515 filed Jul. 7, 2015.

The substituted benzotriazole phenolate salts of this disclosure are not simple salts of the type [anion][cation] such as one would expect for this type of salt. Rather, the salts are macromolecular salt compositions comprising an assembly of metal salts having repeat units of a substituted benzotriazole phenolate anion and metal cation(s) with the general structure: $\{[\text{anion}][\text{cation}]\}_a$ where a is an integer of from two to four. The methods in which this macromolecular composition has been verified will be described in greater detail in the Examples section. Nuclear magnetic resonance (NMR) spectra verifies that the macromolecular structure is present in solution.

The terms "a", "an", and "the" are used interchangeably with "at least one" to mean one or more of the elements being described.

The term "alkyl" refers to a monovalent group that is a radical of an alkane, which is a saturated hydrocarbon. The alkyl can be linear, branched, cyclic, or combinations thereof and typically has 1 to 20 carbon atoms. In some embodiments, the alkyl group contains 1 to 18, 1 to 12, 1 to 10, 1 to 8, 1 to 6, or 1 to 4 carbon atoms. Examples of alkyl groups include, but are not limited to, methyl, ethyl, n-propyl, isopropyl, n-butyl, isobutyl, tert-butyl (t-butyl), n-pentyl, n-hexyl, cyclohexyl, n-heptyl, n-octyl, and ethylhexyl.

The term "alkenyl" refers to a monovalent group that is a radical of an alkene, which is a hydrocarbon with at least one carbon-carbon double bond. The alkenyl can be linear, branched, cyclic, or combinations thereof and typically contains 2 to 20 carbon atoms. In some embodiments, the alkenyl contains 2 to 18, 2 to 12, 2 to 10, 4 to 10, 4 to 8, 2 to 8, 2 to 6, or 2 to 4 carbon atoms. Exemplary alkenyl groups include ethenyl, n-propenyl, and n-butenyl.

The term "alkaryl" as used herein refers to aryl substituted alkyl group of the general structure —R$^a$—Ar, where R$^a$ is an alkylene group and Ar is an aryl group. An example of an alkaryl group is a benzyl group —CH$_2$-Ph.

The term "heteroatom substituted" refers to an alkyl, aryl or other group which contains heteroatoms. These heteroatoms may be pendant atoms, for example, halogens such as fluorine, chlorine, bromine, or iodine or catenary atoms such as nitrogen, oxygen, boron, or sulfur.

The term "alkoxy" refers to a group with the general structure —O—R, where R is an alkyl group. The term "aryloxy" refers to a group with the general structure —O—R, where R is an aryl group. In some instances, the term alkoxy is used generically to describe both alkoxy and aryloxy groups.

The term "aryl" refers to an aromatic carbocyclic group that is a radical containing 1 to 5 rings which may be connected or fused. The aryl group may be substituted with alkyl or heteroalkyl groups. Examples of aryl groups include phenyl groups, naphthalene groups and anthracene groups.

The terms "room temperature" and "ambient temperature" are used interchangeably to mean temperatures in the range of 20° C. to 25° C.

Unless otherwise indicated, all numbers expressing feature sizes, amounts, and physical properties used in the specification and claims are to be understood as being modified in all instances by the term "about." Accordingly, unless indicated to the contrary, the numbers set forth are approximations that can vary depending upon the desired properties using the teachings disclosed herein.

Disclosed herein are compositions of matter comprising salts of substituted benzotriazole phenolate anions and metal cations that are macromolecular salts, and antioxidant compositions comprising one or more macromolecular salts of substituted benzotriazole phenols.

Among the compositions disclosed herein are compositions of matter comprising macromolecular salts of a substituted benzotriazole phenolate anion and a metal cation with repeating units with the structure of Formula I:

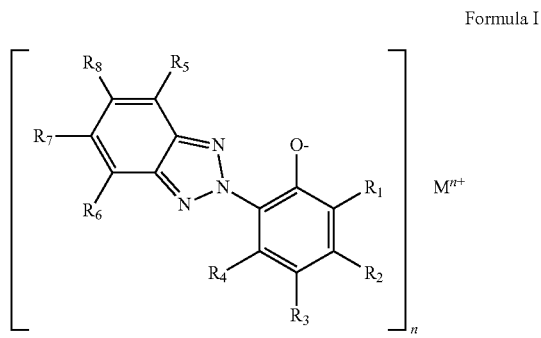

Formula I

In Formula I, at least one of $R^1$ and $R^3$ comprises a substituent group, that is to say a group other than a hydrogen atom. In many embodiments, both $R^1$ and $R^3$ comprise substituent groups. In some embodiments $R^1$ is not substituted i.e. $R^1$ comprises a hydrogen atom, in many other embodiments $R^1$ is a substituent group or another linked benzotriazole phenol group, as will be described in greater detail below.

In embodiments where $R^1$ is not substituted (i.e. is a hydrogen atom), $R^3$ comprises an alkyl, alkoxy or aryloxy group comprising 1-20 carbon atoms, and each $R^2$, $R^4$, $R^5$, $R^6$, $R^7$, and $R^8$, independently comprises a hydrogen atom, an alkyl group, an alkenyl group, an aryl group, or a halogen atom. In one embodiment, $R^1$ comprises a hydrogen atom, $R^3$ comprises an alkyl group with one carbon atom, and each $R^2$, $R^4$, $R^5$, $R^6$, $R^7$, and $R^8$, independently comprises a hydrogen atom. In another embodiment, $R^1$ comprises a hydrogen atom, $R^3$ comprises an alkoxy group comprising 4 carbon atoms, and each $R^2$, $R^4$, $R^5$, $R^6$, $R^7$, and $R^8$, independently comprises a hydrogen atom.

In a wide variety of embodiments $R^1$ comprises a substituent group. In these embodiments, $R^1$ comprises a halogen atom, an alkyl or substituted alkyl group, an alkenyl group, or a group comprising an —O—$R^9$, a —N—$R^9R^{10}$, a —B($OR^{18}$)($OR^{19}$), or a —$SiR^{20}_3$. In these embodiments $R^9$ comprises a hydrogen atom, an alkyl group, an alkenyl group, an aryl group, or a heteroatom-containing group comprising one or more oxygen, nitrogen, sulfur, or phosphorous atoms, and $R^{10}$ comprises a hydrogen atom, an alkyl group, an alkenyl group, an aryl group, or a heteroatom-containing group comprising one or more oxygen, nitrogen, sulfur, or phosphorous atoms, or $R^9$ and $R^{10}$ together with the atoms connecting form a heterocyclic ring structure, each $R^{18}$ and $R^{19}$ is independently a hydrogen atom, an alkyl group, an aryl group, or $R^{18}$ and $R^{19}$ together with the atoms connecting form a heterocyclic ring structure, each $R^{20}$ group is an alkyl group, and each $R^2$, $R^3$, $R^4$, $R^5$, $R^6$, $R^7$, and $R^8$, independently comprises a hydrogen atom, an alkyl group, an alkenyl group, an aryl group, or a halogen atom. Each of these embodiments will be described in greater detail below.

In some embodiments, $R^1$ comprises a relatively small substituent group, one which is of smaller molecular weight and/or steric size relative to the benzotriazole phenol base molecule. In other embodiments, the $R^1$ group is a substituent group that is comparable in size and/or steric size to the benzotriazole phenol base molecule, and is in fact another benzotriazole phenol linked to the benzotriazole phenol base molecule by an oxygen-based, nitrogen-based, or carbon-based linking group. Examples of the first type, where $R^1$ comprises a relatively small substituent group, will be presented first.

In some embodiments, $R^1$ comprises a halogen atom. Suitable halogen atoms include fluorine, bromine, chlorine and iodine. Bromine (Br) and chlorine (Cl) are particularly suitable.

In some embodiments, $R^1$ comprises an alkyl group, an alkenyl group, or a substituted alkyl group. When $R^1$ comprises an alkyl group typically $R^1$ comprises an alkyl group with 1-6 carbon atoms, in one particular embodiment $R^1$ comprises an alkyl group with 4 carbon atoms, generally a tert-butyl group, and $R^3$ is an alkyl group with 4 carbon atoms, typically a tert-butyl group. When $R^1$ comprises an alkenyl group typically $R^1$ comprises an alkenyl group with 1-6 carbon atoms, in one particular embodiment $R^1$ comprises an alkenyl group with 3 carbon atoms, generally a propenyl group, and $R^3$ is an alkyl group with 1 carbon atom, typically a methyl group. When $R^1$ comprises a substituted alkyl group typically $R^1$ comprises an aryl substituted alkyl group with 1-12 carbon atoms, in one particular embodiment $R^1$ comprises an substituted alkyl group with 10 carbon atoms, a 2,2-dimethyl-3-phenyl group, and $R^3$ is an alkyl group with 8 carbon atoms, typically an iso-octyl group.

In some embodiments, where $R^1$ comprises an —O—$R^9$ group wherein $R^9$ comprises an alkyl group with 1-20 carbon atoms, or an aryl group. In many of these embodiments, $R^3$ is also a substituent group, typically $R^3$ is an alkyl group with 1-20 carbon atoms.

In some embodiments, $R^9$ comprises an alkyl group with 1-6 carbon atoms, in one particular embodiment $R^9$ comprises an alkyl group with 4 carbon atoms, and $R^3$ is an alkyl group with 8 carbon atoms, typically an iso-octyl group.

In other embodiments, $R^9$ comprises an aryl group comprising a substituted phenyl group. In some particular embodiments, $R^9$ comprises a 3-methyl phenyl group or a 4-methyl phenyl group, and $R^3$ is an alkyl group with 8 carbon atoms, typically an iso-octyl group.

In another group of embodiments, $R^1$ comprises an —N—$R^9R^{10}$ group. In some of these embodiments, $R^9$ comprises an alkyl group with 1-20 carbon atoms, or an aryl group. In these embodiments, $R^{10}$ independently comprises a hydrogen atom or alkyl group with 1-6 carbon atoms. In many of these embodiments, $R^3$ is also a substituent group, typically $R^3$ is an alkyl group with 1-20 carbon atoms.

In some embodiments, $R^9$ comprises an alkyl group with 1-6 carbon atoms, or an aryl group comprising a 4-alkyl substituted phenyl group, wherein the alkyl substituted group has 1-6 carbon atoms, and $R^{10}$ comprises a hydrogen atom.

In one particular embodiment, $R^9$ comprises an alkyl group with 1 carbon atom (a methyl group), $R^{10}$ comprises a hydrogen atom, and $R^3$ is an alkyl group with 8 carbon atoms, typically an iso-octyl group. In one particular embodiment, $R^9$ comprises an alkyl group with 6 carbon atoms, $R^{10}$ comprises a hydrogen atom, and $R^3$ is an alkyl group with 8 carbon atoms, typically an iso-octyl group. In yet another particular embodiment, $R^9$ comprises a 4-alkyl substituted phenyl group, wherein the alkyl substituted group has 6 carbon atoms (i.e. the group comprises a 4-hexyl phenyl group), $R^{10}$ comprises a hydrogen atom, and $R^3$ is an alkyl group with 8 carbon atoms, typically an iso-octyl group.

In another particular embodiment, $R^1$ comprises a —B(OH)$_2$ group, in other embodiments $R^1$ comprises —B(—O—C(Me)$_2$—C(Me)$_2$—O—), and $R^3$ is an alkyl group with 8 carbon atoms, typically an iso-octyl group.

In another particular embodiment, $R^1$ comprises a —SiR$^{20}_3$ group where $R^{20}$ comprises an alkyl group with 1-6 carbon atoms, in some embodiments $R^{20}$ comprises 3 carbon atoms, typically $R^{20}$ comprises an isopropyl group.

In Formula I, M is a main group or transition metal ion with a valency of n, and n also describes the stoichiometry of the anionic portion of the salt. Typically n is an integer of 1-4. If n is 1, the metal salt M is a monovalent metal ion and the stoichiometry of the anionic portion is 1. If n is 2, the metal salt M is a divalent metal ion and the stoichiometry of the anionic portion is 2, meaning that two anions are present per M ion. Typically, the cationic portion of the macromolecular salt, M, is a metallic cation with a valency of 1 or 2. In embodiments where M is monovalent, the M is lithium, sodium or potassium. In embodiments where M is divalent, there are two equivalents of the anionic portion in the macromolecular salt, and M is calcium, magnesium, or cobalt. In some embodiments, M is a tetravalent metal ion (n=4) or titanium or vanadium.

The salt shown in Formula I is a macromolecular salt, by which it is meant that it is not a simple anion and cation combination, but is a more complex assembly of anions and cations. The salt shown in Formula I is a repeat unit, and the salt comprises from 2 to 4 repeat units. The stoichiometry of the salt (as defined by the value of n) is different from the macromolecular nature of the salt. The stoichiometry merely refers to the charge balance of the salt, whereas the macromolecular nature of the salt refers to the presence of an extended assembly of salts. As was described above, a simple anion-cation salt would be of the type: [anion][cation], whereas the salts of this disclosure are macromolecular salts of the type: {[anion][cation]}$_a$, where a is an integer of from 2 to 4.

As will be explained in greater detail in the Examples section, NMR (nuclear magnetic resonance) can be used to show that the salts are macromolecular assemblies in solution. This NMR evidence is also shown in the FIGURE. To summarize, a characteristic alkyl group on the phenol from which the salt is made shows a single peak. Upon formation of the salt, the single peak forms multiple peaks, demonstrating that the characteristic alkyl group is not a single peak as would be anticipated for a simple [anion][cation] salt. The presence of multiple peaks shows that the characteristic alkyl group on the anion experiences slightly different environments because the anions are part of the macromolecular assembly. Analysis of NMR Diffusion measurements can be used to determine the number of repeat units in the macromolecular assembly (the value of a shown above), which is generally 2-4.

As mentioned above, in other embodiments the $R^1$ group is a substituent group that is comparable in size and/or steric size to the benzotriazole phenolate base molecule, and is in fact another benzotriazole phenolate linked to the benzotriazole phenolate base molecule by an oxygen, nitrogen-based, carbon-based, or sulfur-based linking group. Examples of this second type of compound are described by Formula II below:

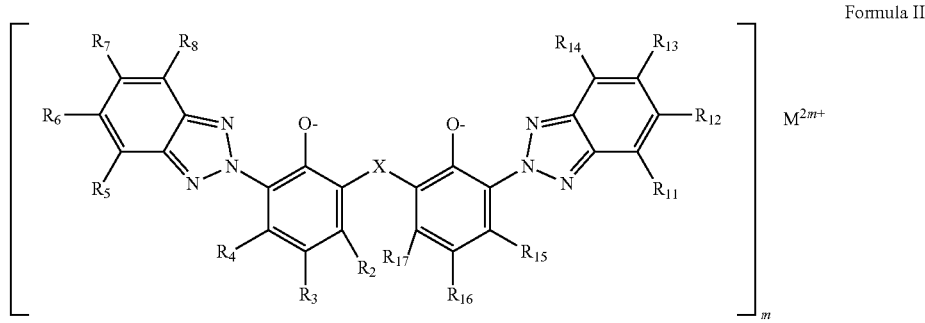

Formula II

The structure of Formula II can be viewed as compound of Formula I where the $R^1$ group is an —X—$R^9$ group an X is a linking group comprising an —O—, —NR$^{10}$—, —S—, —S(O)—, —S(O)$_2$—, or —CH$_2$—, where S(O) is a sulfinyl group S=O, S(O)$_2$ is a sulfonyl group O=S=O, and where $R^{10}$ comprises a hydrogen atom, an alkyl group, or an aryl group. The $R^9$ group in these embodiments is another benzotriazole phenolate group, which may be the same or different from the base benzotriazole phenolate group. In these embodiments, each $R^2$, $R^3$, $R^4$, $R^5$, $R^6$, $R^7$, $R^8$, $R^{11}$, $R^{12}$, $R^{13}$, $R^{14}$, $R^{15}$, $R^{16}$, and $R^{17}$, independently comprises a hydrogen atom, an alkyl group, an alkenyl group, an aryl group, or a halogen atom.

In Formula II, M is a metal ion with a valency of 2m, and m also describes the stoichiometry of the anionic portion of the salt. In this instance, m can be a non-integer number, selected from 0.5, 1.0, or 2. If m is 0.5, the metal salt M is monovalent metal (2m=1) and the stoichiometry of the anionic portion is 0.5 (i.e. one half the anionic portion per M, or 2 M ions per 1 anionic portion). If m is 1, the metal salt M is a divalent metal ion and the stoichiometry of the anionic portion is 1. If m is 2, the metal salt M is a tetravalent metal ion and the stoichiometry of the anionic portion is 2, meaning that two anions are present per M ion. Typically, the cationic portion of the macromolecular salt, M, is a metallic cation with a valency of 1 or 2. In embodiments where M is monovalent, the M is lithium, sodium or potassium. In embodiments where M is divalent, M is calcium, magnesium, or cobalt. In some embodiments, M is a tetravalent metal ion (m=2) or titanium or vanadium.

In some embodiments of the compounds of Formula II, X comprises an —NR$^{10}$-linking group where R$^{10}$ comprises a hydrogen atom, or an alkyl group comprising 1-3 carbon atoms. Typically in these embodiments, the R$^3$ and R$^{16}$ groups are substituent groups, where R$^3$ and R$^{16}$ each comprise an alkyl group with 1-20 carbon atoms. Typically, each R$^2$, R$^4$, R$^5$, R$^6$, R$^7$, R$^8$, R$^{11}$, R$^{12}$, R$^{13}$, R$^{14}$, R$^{15}$, and R$^{17}$, is a hydrogen atom.

In one particular embodiment, X comprises an —NR$^{10}$— linking group where R$^{10}$ comprises a hydrogen atom, the R$^3$ and R$^{16}$ groups are alkyl groups with 8 carbon atoms, typically iso-octyl groups, and each R$^2$, R$^4$, R$^5$, R$^6$, R$^7$, R$^8$, R$^{11}$, R$^{12}$, R$^{13}$, R$^{14}$, R$^{15}$, and R$^{17}$, is a hydrogen atom.

In another particular embodiment, X comprises an —NR$^{10}$— linking group where R$^{10}$ comprises an alkyl group with 1 carbon atom (a methyl group), the R$^3$ and R$^{16}$ groups are alkyl groups with 8 carbon atoms, typically iso-octyl groups, and each R$^2$, R$^4$, R$^5$, R$^6$, R$^7$, R$^8$, R$^{11}$, R$^{12}$, R$^{13}$, R$^{14}$, R$^{15}$, and R$^{17}$, is a hydrogen atom.

In some embodiments of the compounds of Formula II, X comprises an —O— linking group. Typically in these embodiments, the R$^3$ and R$^{16}$ groups are substituent groups, where R$^3$ and R$^{16}$ each comprise an alkyl group with 1-20 carbon atoms. Typically, each R$^2$, R$^4$, R$^5$, R$^6$, R$^7$, R$^8$, R$^{11}$, R$^{12}$, R$^{13}$, R$^{14}$, R$^{15}$, and R$^{17}$, is a hydrogen atom.

In one particular embodiment, X comprises an —O— linking group, the R$^3$ and R$^{16}$ groups are alkyl groups with 8 carbon atoms, typically iso-octyl groups, and each R$^2$, R$^4$, R$^5$, R$^6$, R$^7$, R$^8$, R$^{11}$, R$^{12}$, R$^{13}$, R$^{14}$, R$^{15}$, and R$^{17}$, is a hydrogen atom.

In some embodiments of the compounds of Formula II, X comprises a —S— linking group. Typically in these embodiments, the R$^3$ and R$^{16}$ groups are substituent groups, where R$^3$ and R$^{16}$ each comprise an alkyl group with 1-20 carbon atoms. Typically, each R$^2$, R$^4$, R$^5$, R$^6$, R$^7$, R$^8$, R$^{11}$, R$^{12}$, R$^{13}$, R$^{14}$, R$^{15}$, and R$^{17}$, is a hydrogen atom.

In one particular embodiment, X comprises a —S— linking group, the R$^3$ and R$^{16}$ groups are alkyl groups with 8 carbon atoms, typically iso-octyl groups, and each R$^2$, R$^4$, R$^5$, R$^6$, R$^7$, R$^8$, R$^{11}$, R$^{12}$, R$^{13}$, R$^{14}$, R$^{15}$, and R$^{17}$, is a hydrogen atom.

In some embodiments, X comprises a methylene group —CH$_2$—. Typically in these embodiments, the R$^3$ and R$^{16}$ groups are substituent groups, where R$^3$ and R$^{16}$ each comprise an alkyl group with 1-20 carbon atoms. Typically, each R$^2$, R$^4$, R$^5$, R$^6$, R$^7$, R$^8$, R$^{11}$, R$^{12}$, R$^{13}$, R$^{14}$, R$^{15}$, and R$^{17}$, is a hydrogen atom. In a particular embodiment, R$^3$ and R$^{16}$ each comprise an iso-octyl group. The phenol from which this salt is prepared is commercially available from BASF as TINUVIN 360.

The macromolecular nature of the salt compositions was unexpected and has been shown to be present in solution. The methodology for confirming the macromolecular nature of these salts is described in greater detail in the Examples section below. While not wishing to be bound by theory, it is believed that the unexpected macromolecular structure of the salt composition also impacts the other unexpected properties of these salts, especially their anti-oxidant activity and their fluorescence.

Also disclosed are a new class of antioxidant compositions. These antioxidant compositions comprise at least one of the macromolecular salts described above. These antioxidant compositions are useful in a wide range of applications. Among these applications are the addition of these compositions to polymeric matrices. A wide range of matrices are suitable as are described in application 62/189,493 filed on the same day as the present application.

One particular application for which these salts, macromolecular salts, and antioxidant compositions have been shown to be particularly suitable is as charge additives in electret articles. This is described in application 62/189,515 filed on the same day as the present application.

Descriptions for the preparation of the substituted benzotriazole phenolate salts and the antioxidant compositions prepared from them are described in detail below in the Examples section.

EXAMPLES

These examples are merely for illustrative purposes only and are not meant to be limiting on the scope of the appended claims. All parts, percentages, ratios, etc. in the examples and the rest of the specification are by weight, unless noted otherwise. Solvents were Alfa Aesar (ChemSeal grade) and were used with no further purification. Solvents that were used in separations, isolations, chromatography, and other general use were obtained from EMD (Omnisolv Grade).

The following abbreviations are used throughout the Examples: M=molar; min=minutes; h=hours; equiv=equivalents; x=times; g=grams; mg=milligrams; mmol=millimoles; L=liters; mL=milliliters; rt=room temperature; aq=aqueous; RBF=round bottom flask.

Materials

The following is a table of commercially available materials and reagents that were used.

| Compound | Supplier |
|---|---|
| Bases | |
| sodium ethoxide (ca. 20% in Ethanol) | TCI America |
| sodium tert-butoxide | TCI America |
| n-butyllithium (1.6M in hexanes) | Sigma-Aldrich |
| potassium carbonate | EMD Millipore |
| cesium carbonate | Alfa Aesar |
| potassium hydroxide | EMD Millipore |
| triethylamine | Sigma-Aldrich |
| sodium bicarbonate | Sigma-Aldrich |
| ammonium chloride | VWR |
| Oxidants | |
| 1,3-Dibromo-5,5-dimethylhydantoin | Alfa Aesar |
| hydrogen peroxide, 30% | J.T. Baker |
| urea hydrogen peroxide adduct | Alfa Aesar |
| m-chloroperoxybenzoic acid | Alfa Aesar |
| Ligands | |
| 2-(Dicyclohexylphosphino)-2',4',6'-tri-i-propyl-1,1'-biphenyl (XPhos) | Strem |
| 2-(Di-t-butylphosphino)-3-methoxy-6-methyl-2'-4'-6'-tri-i-propyl-1,1'-biphenyl (RockPhos) | Strem |
| 2-(Di-t-butylphosphino)-3,6-dimethoxy-2',4',6'-tri-i-propyl-1,1'-biphenyl (t-buBrettPhos) | Strem |
| 1,1'bis(diphenylphospino)ferrocene | Strem |
| Catalysts | |
| tris(dibenzylideneacetone)dipalladium | Strem |
| palladium acetate | TCI America |
| allylpalladium(II) chloride dimer | Lancaster |
| copper acetate | Alfa Aesar |
| Methanesulfonato(2-(di-t-butylphosphino)-3,6-dimethoxy-2',4',6'-tri-i-propyl-1,1'-biphenyl)(2'-amino-1,1'-biphenyl-2-yl)palladium(II) (XPhos Precatalyst) | Strem |

-continued

| Compound | Supplier |
|---|---|
| Methanesulfonato(2-(di-t-butylphosphino)-3-methoxy-6-methyl-2',4',6'-tri-i-propyl-1,1'-biphenyl)(2'-amino-1,1'-biphenyl-2-yl)palladium(II) (RockPhos Precatalyst) | Strem |
| Methanesulfonato(2-(di-t-butylphosphino)-3,6-dimethoxy-2',4',6'-tri-i-propyl-1,1'-biphenyl)(2'-amino-1,1'-biphenyl-2-yl)palladium(II) (t-BuBrettPhos Precatalyst) | Strem |
| Reagents | |
| p-tolylboronic acid | Aldrich Chemical |
| trimethylborate | Alfa Aesar |
| iodomethane | Alfa Aesar |
| triisopropylchlorosilane | Alfa Aesar |
| boron tribromide | Sigma-Aldrich |
| thionyl chloride | Alfa Aesar |
| trifluoromethanesulfonic anhydride | Oakwood |
| 2-(2H-Benzotriazol-2-yl)-4-(1,1,3,3-tetramethylbutyl)phenol | TCI America |
| m-cresol | Alfa Aesar |

-continued

| Compound | Supplier |
|---|---|
| n-butanol | Sigma-Aldrich |
| methylamine hydrochloride | Aldrich Chemical |
| 4-n-hexylaniline | Alfa Aesar |
| hexylamine | Alfa Aesar |
| ammonia (0.5M in dioxane) | Sigma Aldrich |
| scandium triflate | Strem |
| 4-methylbenzenethiol toluene | Alfa Aesar |
| potassium thioacetate | Alfa Aesar |
| 3,5-bis(trifluoromethyl)aniline | Alfa Aesar |
| 1-bromo-4-(heptadecafluorooctyl)benzene | Sigma Aldrich |
| 1-iodooctadecane | Alfa Aesar |

Structural Formulas of Phenol and Protected Phenol (Ether) Compounds Disclosed.

The table below presents a summary of the structural formulas for the phenol compounds used in this application to prepare phenolate salts. The phenols are either commercially available or prepared in the Synthesis Examples below.

TABLE A

Listing of Phenol Structures

| Name | Source | Structure |
|---|---|---|
| Ether-1 | Synthesis Example SE2 | *[structure: 2H-benzotriazol-2-yl group attached to a phenyl ring bearing OMe, Br, and a 1,1,3,3-tetramethylbutyl substituent]* |
| Phenol-1 | Commercially available | *[structure: 2-(2H-benzotriazol-2-yl)-4-methylphenol]* |
| Phenol-2 | Commercially Available | *[structure: 2-(2H-benzotriazol-2-yl)-4-methyl-6-allylphenol]* |
| Phenol-3 | Synthesis Example SE1 | *[structure: 2-(2H-benzotriazol-2-yl)phenol with n-C4 O-substituent]* |

TABLE A-continued

Listing of Phenol Structures

| Name | Source | Structure |
|---|---|---|
| Phenol-4 | Commercially Available | 6-chlorobenzotriazol-2-yl attached to 2-hydroxy-3,5-di-t-butylphenyl |
| Phenol-5 | Synthesis Example SE2 | benzotriazol-2-yl attached to 2-hydroxy-3-bromo-5-(iso-C8)phenyl |
| Phenol-6 | Synthesis Example SE3 | benzotriazol-2-yl attached to 2-hydroxy-3-(tri-isopropylsilyl)-5-(iso-C8)phenyl |
| Phenol-7 | Synthesis Example SE4 | benzotriazol-2-yl attached to 2-hydroxy-3-(n-C4-oxy)-5-(iso-C8)phenyl |
| Phenol-8 | Synthesis Example SE5 | benzotriazol-2-yl attached to 2-hydroxy-3-(n-C6-amino)-5-(iso-C8)phenyl |
| Phenol-9 | Synthesis Example SE6 | benzotriazol-2-yl attached to 2-hydroxy-3-(3-methylphenoxy)-5-(iso-C8)phenyl |

TABLE A-continued

Listing of Phenol Structures

| Name | Source | Structure |
|---|---|---|
| Phenol-10 | Commercially Available | 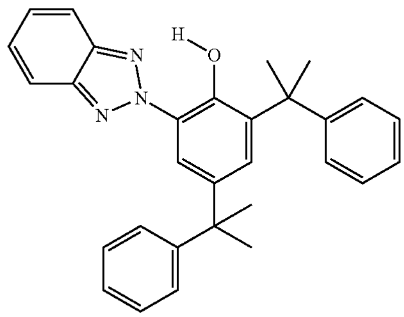 [SMILES: CC(C)(c1ccccc1)c1cc(-n2nc3ccccc3n2)c(O)c(C(C)(C)c2ccccc2)c1] |
| Phenol-11 | Synthesis Example SE7 | 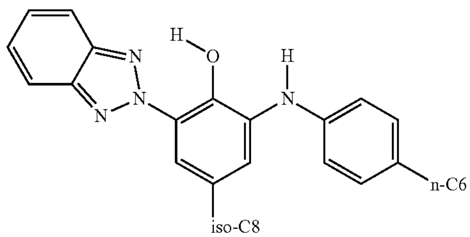 |
| Phenol-12 | Commercially Available | 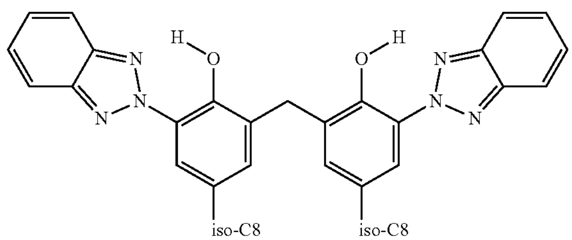 |
| Phenol-13 | Synthesis Example SE8 | 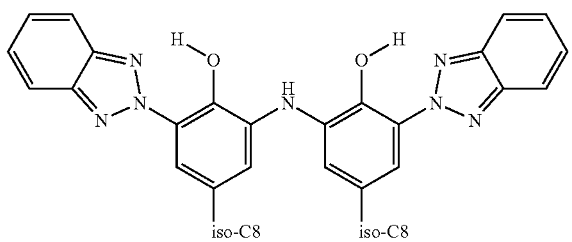 |
| Phenol-14 | Synthesis Example SE9 | 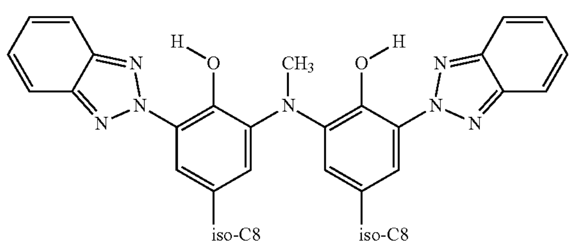 |
| Phenol-15 | Synthesis Example SE10 | 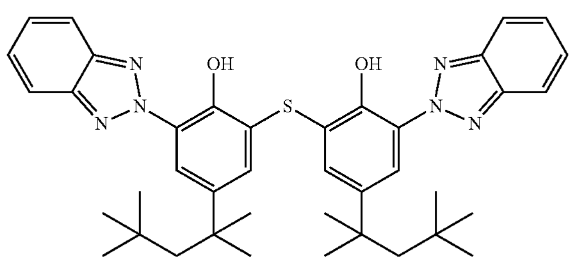 |

TABLE A-continued

Listing of Phenol Structures

| Name | Source | Structure |
|------|--------|-----------|
| Phenol-16 | Commercially Available | 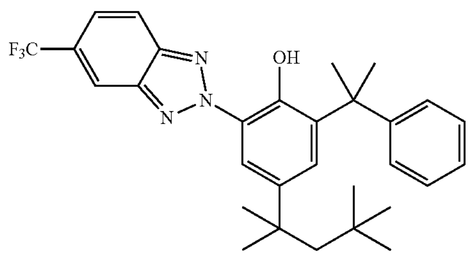 [SMILES: CC(C)(C)CC(C)(C)c1cc(-n2nc3ccc(C(F)(F)F)cc3n2)c(O)c(C(C)(C)c2ccccc2)c1] |
| Phenol-17 | Synthesis Example SE11 | 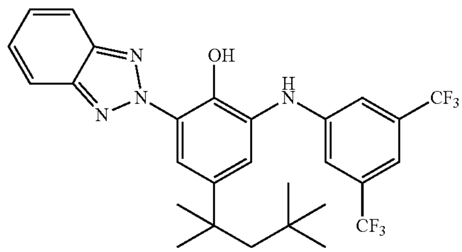 [SMILES: CC(C)(C)CC(C)(C)c1cc(Nc2cc(C(F)(F)F)cc(C(F)(F)F)c2)c(O)c(-n2nc3ccccc3n2)c1] |
| Phenol-18 | Synthesis Example SE12 | 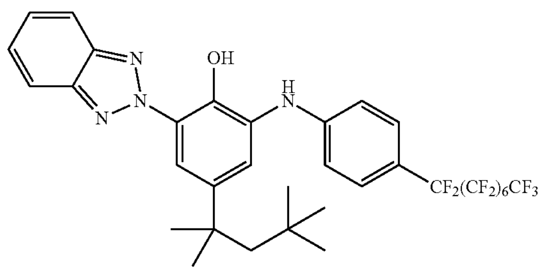 |
| Phenol-19 | Synthesis Example SE13 | 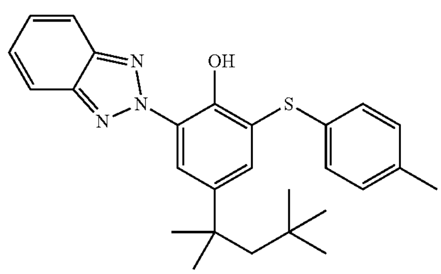 [SMILES: Cc1ccc(Sc2cc(C(C)(C)CC(C)(C)C)cc(-n3nc4ccccc4n3)c2O)cc1] |
| Phenol-20 | Synthesis Example SE14 | 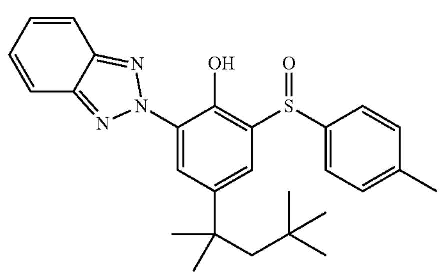 [SMILES: Cc1ccc(S(=O)c2cc(C(C)(C)CC(C)(C)C)cc(-n3nc4ccccc4n3)c2O)cc1] |

TABLE A-continued

Listing of Phenol Structures

| Name | Source | Structure |
|---|---|---|
| Phenol-21 | SynthesisExample SE15 | 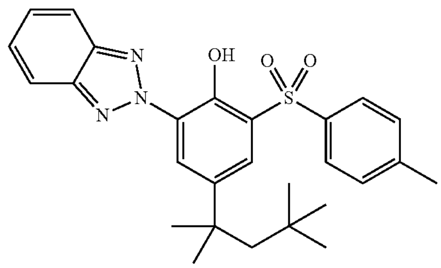 [SMILES: Cc1ccc(S(=O)(=O)c2cc(C(C)(C)CC(C)(C)C)cc(-n3nc4ccccc4n3)c2O)cc1] |
| Phenol-22 | Synthesis Example SE16 | 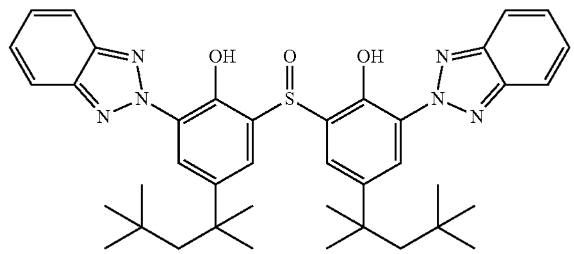 [SMILES: CC(C)(C)CC(C)(C)c1cc(-n2nc3ccccc3n2)c(O)c(S(=O)c2cc(C(C)(C)CC(C)(C)C)cc(-n3nc4ccccc4n3)c2O)c1] |
| Phenol-23 | Synthesis Example SE17 | 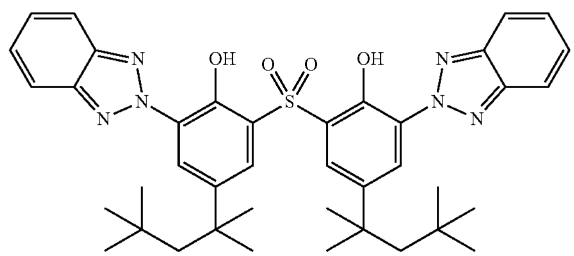 [SMILES: CC(C)(C)CC(C)(C)c1cc(-n2nc3ccccc3n2)c(O)c(S(=O)(=O)c2cc(C(C)(C)CC(C)(C)C)cc(-n3nc4ccccc4n3)c2O)c1] |
| Phenol-24 | Synthesis Example SE18 | 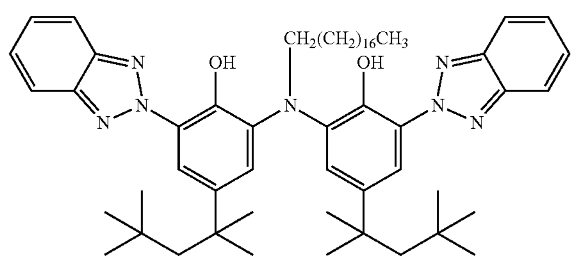 |

General Synthesis of Phenols

In the examples below automated flash chromatography (AFC) was carried out using an ISOLERA system available from Biotage, Inc, Charlottesville, Va., USA. For these purifications Biotage SNAP Ultra silica columns were used with a hexane/ethyl acetate gradient mixture.

All intermediates and products were confirmed using $^1$H and $^{13}$C Nuclear Magnetic Resonance (NMR) on a 500 MHz Bruker instrument. In some cases HRMS was also obtained.

A specialized reaction was used to prepare Phenol-3 as shown in Synthesis Example SE1 below, for the other phenols synthesized, General Reaction Scheme I was followed.

Synthesis Example SE1: Phenol-3

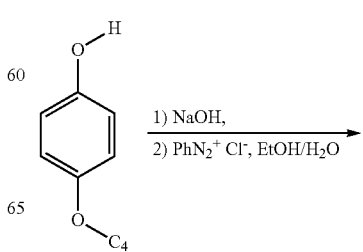

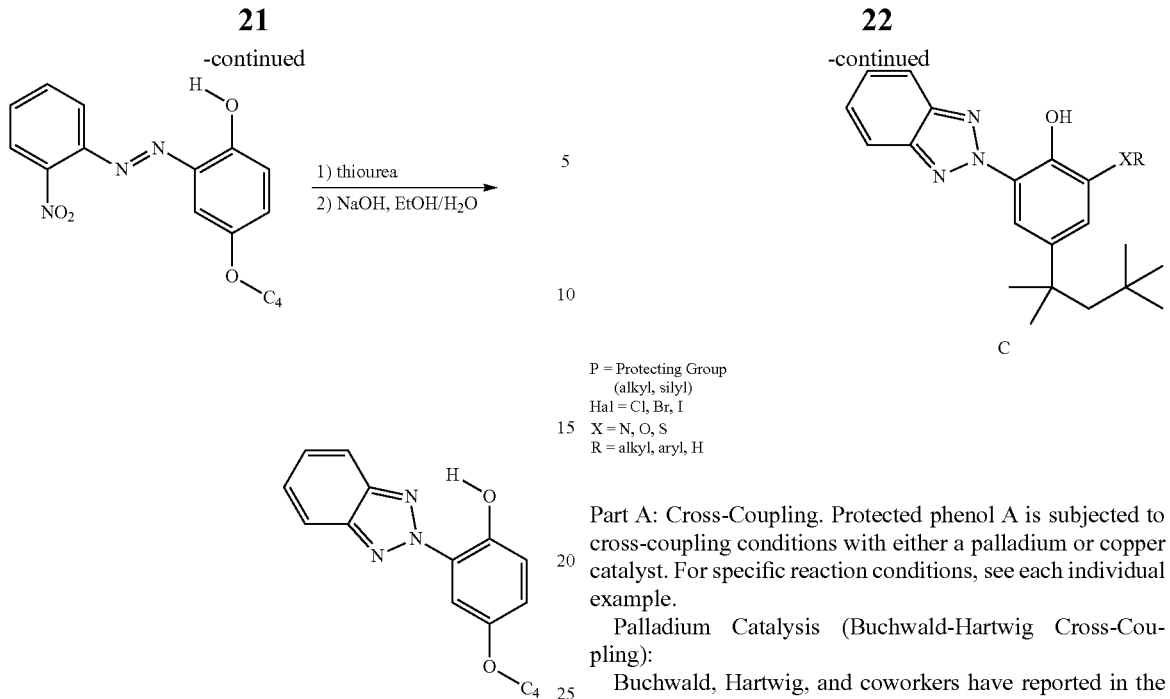

The diazo compound above as synthesized following standard diazotization procedure (WO008131921; *Bioorg. Med. Chem. Lett.* 2010, 20, 4193-4195.), followed by reductive cyclization to give Phenol-3.

A General Reaction Scheme I is presented below which was followed to prepare the a number of phenols used to prepare the phenolate salts of this disclosure. Specific details are provided for each Synthesis Example.

General Reaction Scheme I.

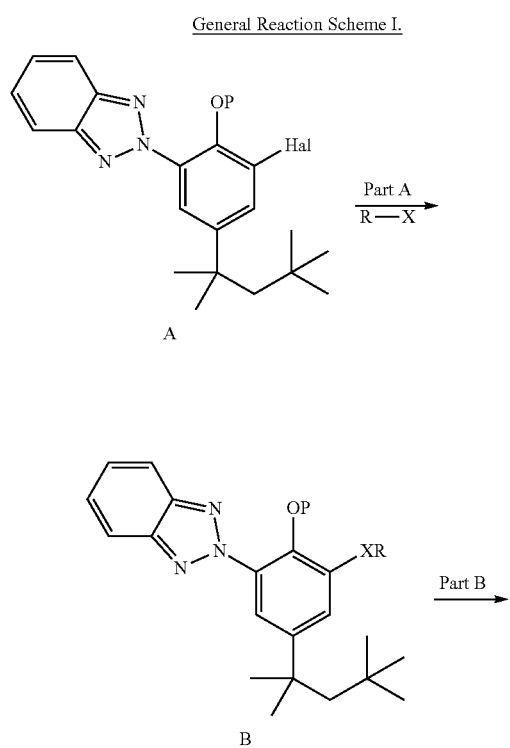

P = Protecting Group (alkyl, silyl)
Hal = Cl, Br, I
X = N, O, S
R = alkyl, aryl, H Part A: Cross-Coupling. Protected phenol A is subjected to cross-coupling conditions with either a palladium or copper catalyst. For specific reaction conditions, see each individual example.

Palladium Catalysis (Buchwald-Hartwig Cross-Coupling):

Buchwald, Hartwig, and coworkers have reported in the literature a transformation in which aryl halides can be converted to heteroatoms by use of a palladium catalyst and a bulky phosphine ligand. The following commercially available ligands (developed by Buchwald) have been used to synthesize benzotriazole phenolic analogs in which a heteroatom has been introduced in the ortho position (see compound B). These ligands can also be purchased already complexed to the palladium catalyst and are referred to as precatalysts.

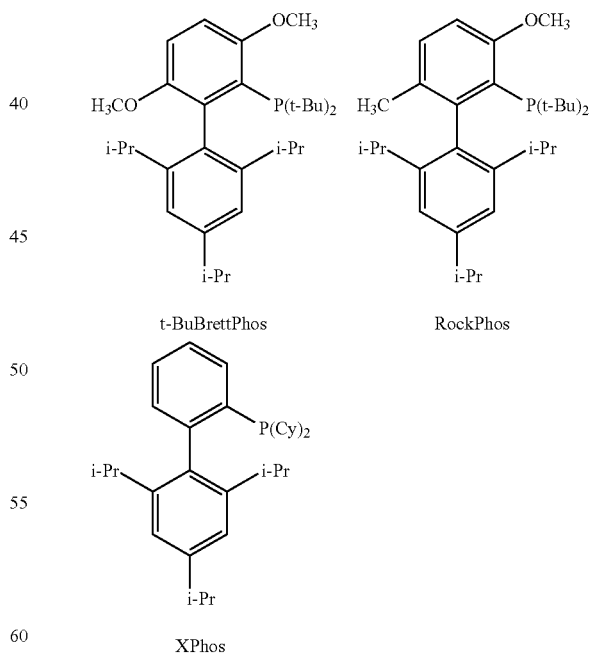

Copper Catalysis (Chan-Evans-Lam Coupling):

Copper can also be used to effect cross-coupling reactions between arylboronic acids and phenols, anilines, or arylthiols. This is considered to be a modification of the Ullmann condensation, as described in Kürti, L.; Czakó. *Strategic*

Applications of Named Reactions in Organic Synthesis, 1st ed. Burlington: MA, 2005, pp. 464-465. The reaction is stoichiometric in copper salts and is typically performed under ambient conditions.

Part B: Deprotection of Methyl Ether. The methoxy ether benzotriazole (B, P=Me) was dissolved in dichloromethane (0.1 M) and cooled to −78° C. while stirring under $N_2$. Boron tribromide (1 equivalent per protected phenol) was added dropwise and the reaction mixture allowed to slowly warm to room temperature. When the reaction was complete (analysis by TLC), water was added dropwise and the mixture was stirred for 10 min. The organic layer was separated and the aqueous layer extracted with DCM (2×). The combined organic layers were washed with saturated aqueous $NaHCO_3$ and brine, dried ($Na_2SO_4$ or $MgSO_4$), filtered and concentrated. The residue was purified ($SiO_2$) to give products in 78-98% yield.

Note that in the following Synthesis Examples, compounds that are referred to as "Ethers" are protected phenols, meaning that the —OH group is instead a "protected hydroxyl group" i.e. a —$OCH_3$ group, which is deprotected to reform the phenolic hydroxyl group.

Synthesis Example SE2: Ether-1 and Phenol-5

2-(3-bromo-2-methoxy-5-(2,4,4-trimethylpentan-2-yl)phenyl)-2H-1,2,3-benzotriazole

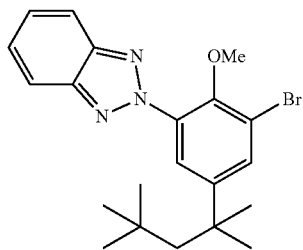 [SMILES: COc1c(Br)cc(C(C)(C)CC(C)(C)C)cc1-n1nc2ccccc2n1]

Part A: Bromination. 2-(2H-Benzotriazol-2-yl)-4-(1,1,3,3-tetramethylbutyl)phenol (100 g, 309 mmol) was placed in a 1 L round bottom flask fitted with a stir bar and dissolved in chloroform (500 mL). To this was added 1,3-dibromo-5,5-dimethylhydantoin (DBDMH) (45.95 g, 161 mmol) and the mixture stirred rt overnight. After such time, the mixture was filtered and concentrated to give a dark red residue. The residue was recrystallized from dichloromethane/ethanol to obtain white crystals. Multiple recrystallizations of the mother liquor yielded 113 g of pure product (91% yield) of Phenol-5.

Part B: Methylation. The reaction product from Part A was placed in a 1 L round bottom flask fitted with a stir bar and dissolved in acetonitrile (400 mL). Potassium carbonate (20.70 g, 150 mmol) was added followed by iodomethane (3.3 mL, 52.5 mmol). The mixture stirred rt overnight. After such time, the reaction mixture was partially concentrated, diluted with ethyl acetate and filtered over celite. The solution was concentrated, giving a thick beige oil, which eventually solidified over time to give 20.8 g (quantitative yield) of product of Ether 1.

Synthesis Example SE3: Phenol-6

2-(2H-1,2,3-benzotriazol-2-yl)-6-((triisopropylsilyl)oxy)-4-(2,4,4-trimethylpentan-2-yl)phenol

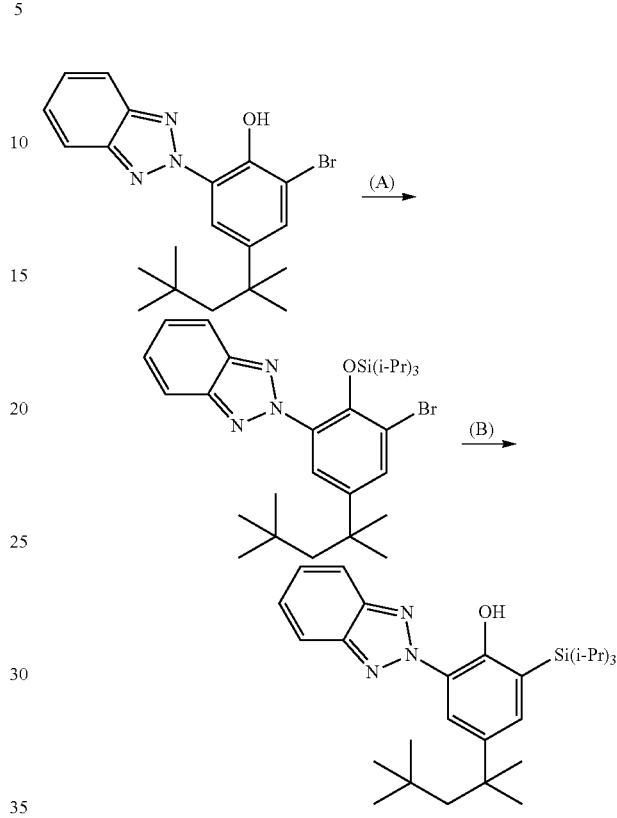

Part A. The reaction product from Synthesis Example SE2 was silylated with triisopropylchlorosilane (TIPS-Cl) following standard procedures.

Part B. The reaction product from Part A (1.57 g, 2.81 mmol) was placed into a round bottom flask containing a stir bar and charged with $N_2$. THF (20 mL) was added and the flask cooled to −78° C. n-Butyl lithium (1.8 mL, 2.81 mmol) was added and the mixture was allowed to slowly warm to rt and stir for 3 h. After such time, the reaction was quenched with saturated ammonium chloride and the product extracted with EtOAc (3×). The combined organic layers were washed with brine, dried and filtered. The crude residue was purified by AFC to give a colorless solid (0.74 g, 55% yield).

Synthesis Example SE4: Phenol-7

2-(2H-1,2,3-benzotriazol-2-yl)-6-butoxy-4-(2,4,4-trimethylpentan-2-yl)phenol

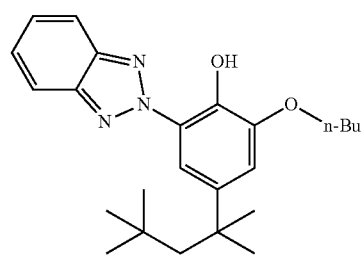

Into three flame dried 40-dram vials, each equipped with a stir bar and activated 4 Å molecular sieves was placed Ether 1 prepared in Synthesis Example SE1, (4.179 g, 10.04 mmol), cesium carbonate (4.91 g, 15.06 mmol), allylpalladium chloride dimer (18.4 mg, 0.5 mol %), and RockPhos ligand (23.4 mg, 0.5 mol %). Each vial was fitted with a septa cap and evacuated and backfilled with $N_2$ (3×). Toluene (10 mL), followed by anhydrous n-butanol (1.8 mL, 20.08 mmol) was added to each vial. The vials were placed on a ChemGlass reaction block and heated to 100° C. for 72 h. After such time, the reaction mixtures were combined, filtered over celite, and concentrated. The crude residue was purified via flash column chromatography to give a pale yellow solid (9.80 g, 79% yield). Following Part B (General Reaction Scheme I), the free phenol was isolated as a beige solid after purification by flash column chromatography (8.50 g, 85% yield).

Synthesis Example SE5: Phenol-8

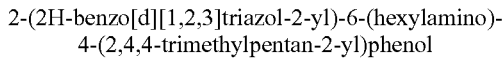

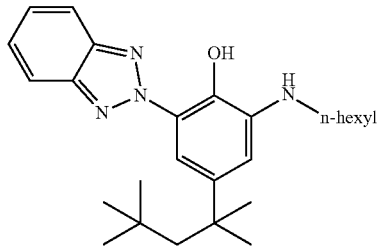

Into three flame dried vials equipped with a stir bar was placed Ether 1 prepared in Synthesis Example SE1, (1.66 g, 4 mmol), tris(dibenzylideneacetone)dipalladium(0) (73.3 mg, 0.08 mmol), XPhos ligand (95.3 mg, 0.2 mmol), sodium tert-butoxide (538 mg, 5.6 mmol), and 1-hexylamine (0.74 mL, 5.6 mmol). The vial was fitted with a septa cap and evacuated and backfilled with $N_2$. Dioxane (20 mL) was added and the reaction was heated to 130° C. for 16 h. After such time, the mixtures were cooled to rt, combined, diluted with EtOAc and filtered over celite. The residue was purified via AFC. A beige solid was isolated (3.88 g, 74% yield). Following Part B (General Reaction Scheme I), gave the free phenol as a yellow solid (3.32, 88% yield).

Synthesis Example SE6: Phenol-9

2-(2H-1,2,3-benzotriazol-2-yl)-6-(m-tolyloxy)-4-(2,4,4-trimethlpentan-2-yl)phenol

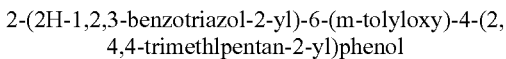

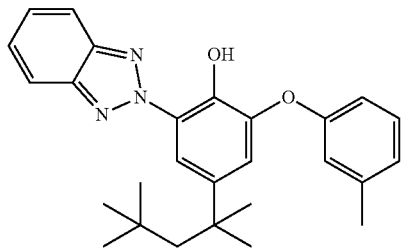 [SMILES: Cc1cccc(Oc2cc(C(C)(C)CC(C)(C)C)cc(-n3nc4ccccc4n3)c2O)c1]

Into two flame dried 40-dram vials, each equipped with a stir bar and activated 4 Å mol sieves was placed Ether 1 prepared in Synthesis Example SE1, (4.16 g, 10 mmol), potassium phosphate (4.25 g, 20 mmol), palladium(II) acetate (45 mg, 2 mol %), and RockPhos ligand (93 mg, 2 mol %). Each vial was fitted with a septa cap and evacuated and backfilled with $N_2$ (3×). Toluene (10 mL), followed by m-cresol (1.3 mL, 12 mmol) was added to each vial. The vials were placed on a ChemGlass reaction block and heated to 100° C. for 16 h. After such time, the reaction mixtures were combined, filtered over celite, and concentrated. The crude residue was purified via flash column chromatography to give a beige solid (7.07 g, 80% yield). Following Part B (General Reaction Scheme I), the free phenol was isolated as a beige solid after purification by flash column chromatography (6.50 g, 98% yield).

Synthesis Example SE7: Phenol-11

2-(2H-benzo[d][1,2,3]triazol-2-yl)-6-((4-hexylphenyl)amino)-4-(2,4,4-trimethylpentan-2-yl)phenol

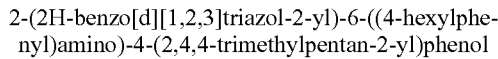

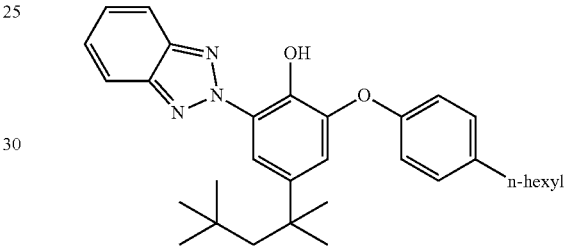

Into three flame dried vials equipped with a stir bar was placed Ether 1 prepared in Synthesis Example SE1, (1.66 g, 4 mmol), tris(dibenzylideneacetone)dipalladium(0) (73.3 mg, 0.08 mmol), XPhos ligand (95.3 mg, 0.2 mmol), sodium tert-butoxide (538 mg, 5.6 mmol), and 4-hexylaniline (1 mL, 5.6 mmol). The vial was fitted with a septa cap and evacuated and backfilled with $N_2$. Dioxane (20 mL) was added and the reaction was heated to 130° C. for 16 h. After such time, the mixtures were cooled to rt, combined, diluted with EtOAc and filtered over celite. The residue was purified via AFC. A beige solid was isolated (3.88 g, 74% yield). Following Part B (General Reaction Scheme I), gave the free phenol as a yellow solid (4.67 g, 96% yield).

Synthesis Example SE8: Phenol-13

6,6'-azanediylbis(2-(2H-benzo[d][1,2,3]triazol-2-yl)-4-(2,4,4-trimethylpentan-2-yl)phenol)

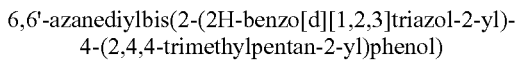

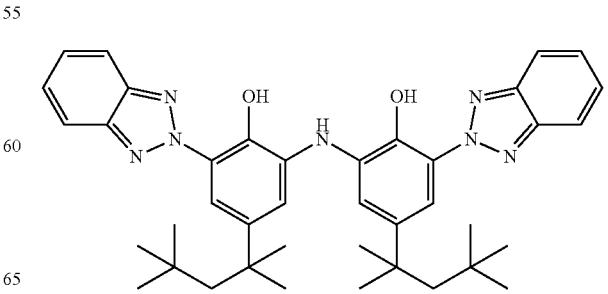

Part A. To an oven-dried Schlenk flask fitted with a stir bar was added 4 Å molecular sieves, sodium tert-butoxide (23.37 mmol, 2.25 g), Pd$_2$(dba)$_3$ (0.33 mmol, 306 mg), XPhos (0.83 mmol, 398 mg) and Ether 1 prepared in Synthesis Example SE1, (16.69 mmol, 6.95 g). The flask was then evacuated and flushed with N$_2$ (3×) and ammonia in dioxane (0.5 M, 100 mL) was added via cannula. The Schlenk flask was closed and heated to 130° C. for 16 h. After such time, the reaction mixture was diluted with EtOAc, filtered, and concentrated. The crude oil was purified via flash column chromatography to give a beige solid.

Part B. The product of Part A was dissolved in dichloromethane (150 mL) and cooled to −78° C. while stirring under N$_2$. Boron tribromide (17.10 mmol, 1.6 mL) was added dropwise and the reaction mixture allowed to slowly warm to rt. When the reaction was complete (analysis by TLC), water was added dropwise and the mixture was stirred for 10 min. The organic layer was separated and the aqueous layer extracted with DCM (2×). The combined organic layers were washed with saturated aqueous NaHCO$_3$ and brine, dried (Na$_2$SO$_4$ or MgSO$_4$), filtered and concentrated. The residue was recrystallized from hot acetone to give a yellow crystalline solid (3.38 g, 61% yield from Ether 1).

Synthesis Example SE9: Phenol-14

6,6'-(methylazanediyl)bis(2-(2H-benzo[d][1,2,3]triazol-2-yl)-4-(2,4,4-trimethylpentan-2-yl)phenol)

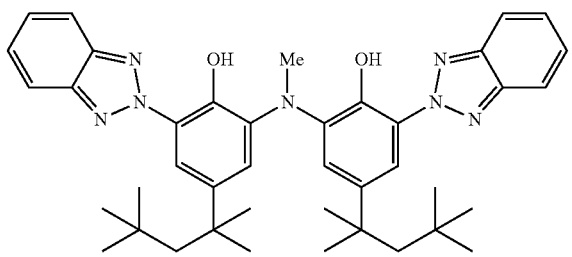 [SMILES: CN(c1cc(C(C)(C)CC(C)(C)C)cc(-n2nc3ccccc3n2)c1O)c1cc(C(C)(C)CC(C)(C)C)cc(-n2nc3ccccc3n2)c1O]

Part A. The reaction product from Synthesis Example SE6, Part A (12.79 mmol, 8.8 g) was dissolved in dimethylformamide (120 mL) and to this, sodium hydride (14.07 mmol, 0.56 g) was added under a stream of N$_2$ at rt. The mixture was stirred 10 min and then iodomethane (14.07 mmol, 0.88 mL) was added and stirring continued for another 2 h. The reaction was quenched with saturated aq ammonium chloride and extracted with EtOAc (3×). The combined organic layers were washed with water and then brine, dried with Na$_2$SO$_4$, filtered and concentrated. No further purification was performed.

Part B. The product of Part B was dissolved in dichloromethane (150 mL) and cooled to −78° C. while stirring under N$_2$. Boron tribromide (17.10 mmol, 1.6 mL) was added dropwise and the reaction mixture allowed to slowly warm to rt. When the reaction was complete (analysis by TLC), water was added dropwise and the mixture was stirred for 10 min. The organic layer was separated and the aqueous layer extracted with DCM (2×). The combined organic layers were washed with saturated aqueous NaHCO$_3$ and brine, dried (Na$_2$SO$_4$ or MgSO$_4$), filtered and concentrated. The residue was recrystallized from hot acetone to give a yellow crystalline solid (6.74 g, 60% yield from Ether 1).

Synthesis Example SE10: Phenol-15

6,6'-thiobis(2-(2H-benzo[d][1,2,3]triazol-2-yl)-4-(2,4,4-trimethylpentan-2-yl)phenol)

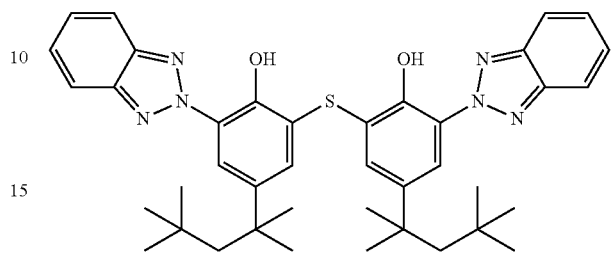

To a flame dried vial equipped with a stir bar was placed 3-bromo-2-methoxy-5-(2,4,4-trimethylpentan-2-yl)phenyl)-2H-1,2,3-benzotriazole (0.416 g, 1 mmol), potassium thioacetate (0.057 g, 0.5 mmol), Tris(dibenzylideneacetone)dipalladium(0) (0.023 g, 0.025 mmol), 1,1'-Bis(diphenylphosphino)ferrocene (0.028 g, 0.05 mmol) and potassium phosphate (0.127 g, 0.6 mmol). The vial was then evacuated and flushed with N2 (3×) and toluene (0.5 mL) and acetone (0.25 mL) was added. The reaction mixture was stirred for 72 h at 130° C. After such time, the mixture was cooled, filtered, and purified by flash column chromatography to obtain 5 as a white solid (0.240 g, 68% yield). Following the procedure from Example 10, Part B, the product was obtained as a white solid (0.230 g, 99% yield).

Synthesis Example SE11: Phenol 17

2-(2H-benzotriazol-2-yl)-6-((3,5-bis(trifluoromethyl)phenyl)amino)-4-(2,4,4-trimethylpentan-2-yl)phenol

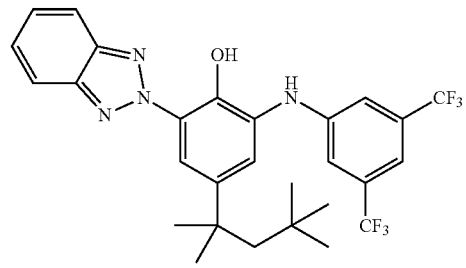 [SMILES: CC(C)(C)CC(C)(C)c1cc(Nc2cc(C(F)(F)F)cc(C(F)(F)F)c2)c(O)c(-n2nc3ccccc3n2)c1]

Into a 250 mL Schlenk flask equipped with a stir bar was placed Ether-1 from SE2, (20.0 g, 48.03 mmol), tris(dibenzylideneacetone)dipalladium(0) (1.04 g, 1.14 mmol), XPhos ligand (1.35 g, 2.75 mmol), sodium tert-butoxide (7.63 g, 79.4 mmol), and 3,5-bis(trifluoromethyl)aniline (8 mL, 51.36 mmol). The Schlenk flask evacuated and backfilled with N$_2$. Dioxane (200 mL) was added and the reaction was heated to 130° C. for 16 h. After such time, the mixture was cooled to rt, diluted with EtOAc, filtered over celite and concentrated. The residue was purified via AFC. A brown solid was isolated (26.8 g, 98% yield). Following Part B (General Reaction Scheme I), gave the free phenol as a yellow solid (21.3 g, 82% yield).

Synthesis Example SE12: Phenol 18

2-(2H-triazol-2-yl)-6-((4-(perfluorooctyl)phenyl)amino)-4-(2,4,4-trimethylpentan-2-yl)phenol

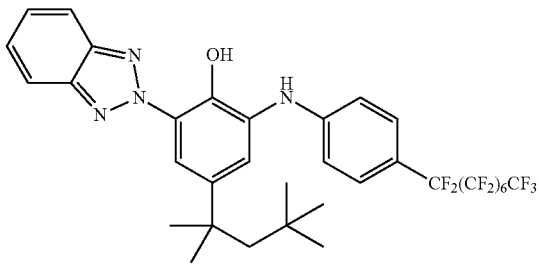

Into two flame dried 40-dram vials, each equipped with a stir bar was placed the aniline side product (3-(2H-benzo[d][1,2,3]triazol-2-yl)-2-methoxy-5-(2,4,4-trimethylpentan-2-yl)aniline) from SE8, Part A (1.162 g, 3.30 mmol), 1-bromo-4-(heptadecafluorooctyl)benzene (2.0 g, 3.30 mmol), tris(dibenzylideneacetone)dipalladium(0) (60.4 mg, 0.066 mmol), XPhos ligand (80 mg, 0.163 mmol), and sodium tert-butoxide (444 mg, 4.62 mmol). Each vial was fitted with a septa cap and evacuated and backfilled with $N_2$. Dioxane (20 mL) was added to each vial and the vials were placed on a ChemGlass reaction block and heated to 130° C. for 16 h. After such time, the mixtures were cooled to rt, diluted with EtOAc, combined, and filtered over celite and concentrated. The residue was purified via AFC. A brown solid was isolated (4.41 g, 79% yield). Following Part B (General Reaction Scheme I), gave the free phenol as a yellow solid (3.41 g, 79% yield).

Synthesis Example SE13: Phenol 19

2-(2H-benzotriazol-2-yl)-6-(p-tolylthio)-4-(2,4,4-trimethylpentan-2-yl)phenol benzotriazole

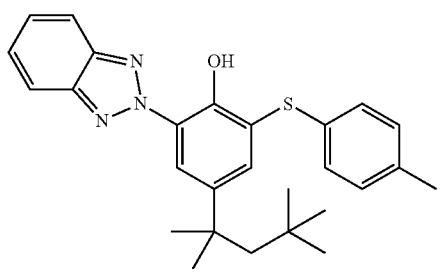 [SMILES: Cc1ccc(Sc2cc(C(C)(C)CC(C)(C)C)cc(-n3nc4ccccc4n3)c2O)cc1]

Into a flame dried vial equipped with a stir bar was placed 2-(2H-benzo[1,2,3]triazol-2-yl)-6-bromo-4-(2,4-dimethylpentan-2-yl)phenol (2.88 g, 6.92 mmol), tris(dibenzylideneacetone)dipalladium(0) (0.317 g, 0.346 mmol), 1,1'bis(diphenylphospino)ferrocene (0.383 g, 0.692 mmol), potassium phosphate (1.76 g, 8.30 mmol), and 4-methylbenzenethiol toluene (1.031 g, 8.30 mmol). The vial was fitted with a septa cap and evacuated and backfilled with $N_2$. Toluene (14 mL) was added and the reaction was heated to 110° C. for 16 h. After such time, the mixtures were cooled to rt, combined, diluted with EtOAc and filtered over celite. The residue was purified via AFC. A beige solid was isolated (3.09 g, 97% yield). Following Part B (General Reaction Scheme I), gave the free phenol as an ivory-colored solid (2.70 g, 90% yield).

Synthesis Example SE14: Phenol 20

2-(2H-benzotriazol-2-yl)-6-(p-tolylsulfinyl)-4-(2,4,4-trimethylpentan-2-yl)phenol

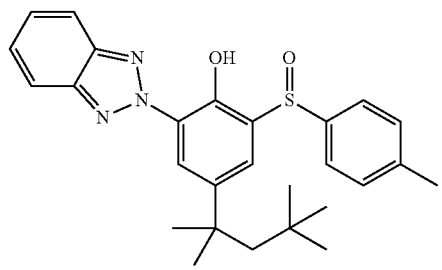 [SMILES: Cc1ccc(S(=O)c2cc(C(C)(C)CC(C)(C)C)cc(-n3nc4ccccc4n3)c2O)cc1]

The following was adapted from a literature procedure (Org Lett. 2003, 5, 235). Aryl sulfide from SE13 (1.2 g, 2.69 mmol) was added to a vial equipped with a stir bar. Ethanol (7 mL) and hydrogen peroxide (30%, 1.5 mL) were added and $N_2$ was bubbled through the mixture for several minutes. Scandium triflate (0.265 g, 0.539 mmol) was added and the mixture allowed to stir rt overnight. After such time, the reaction was quenched with $H_2O$ (2 mL) and filtered. The filtrate was purified by AFC and a white solid was obtained (0.764 g, 61% yield). Another 0.167 g of recrystallized product from the mother liquor was obtained for a total of 0.931 g (75% yield) of product.

Synthesis Example SE15: Phenol 21

2-(2H-benzotriazol-2-yl)-6-tosyl-4-(2,4,4-trimethylpentan-2-yl)phenol

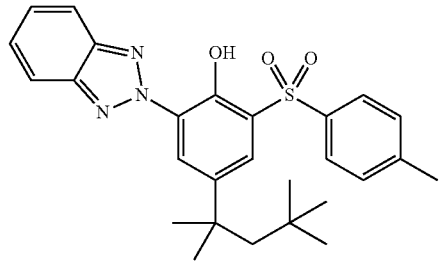 [SMILES: Cc1ccc(S(=O)(=O)c2cc(C(C)(C)CC(C)(C)C)cc(-n3nc4ccccc4n3)c2O)cc1]

Aryl sulfide from SE13 (1.5 g, 3.366 mmol) was dissolved in dichloromethane (17 mL) in a vial equipped with a stir bar. M-Chloroperoxybenzoic acid, 50 wt % (2.56 g, 7.40 mmol) was added and the reaction stirred until complete by TLC. The reaction was then quenched with sat'd aqueous $NaHCO_3$ and the organic layer separated, dried ($Na_2SO_4$), filtered, and concentrated. It was purified by washing with EtOAc and filtering. A white solid was obtained (1.34 g, 83% yield).

Synthesis Example SE16: Phenol 22

6,6'-thiobis(2-(2H-benzo[d][1,2,3]triazol-2-yl)-4-(2,4,4-trimethylpentan-2-yl)phenol)

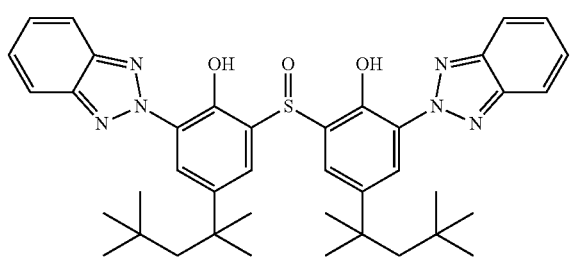 [SMILES: CC(C)(C)CC(C)(C)c1cc(-n2nc3ccccc3n2)c(O)c(S(=O)c2cc(C(C)(C)CC(C)(C)C)cc(-n3nc4ccccc4n3)c2O)c1]

6,6'-Thiobis(2-(2H-benzotriazol-2-yl)-4-(2,4,4-trimethylpentan-2-yl)phenol) from SE10 was oxidized using a literature procedure (Org Lett, 1999, 1, 189). 6,6'-Thiobis(2-(2H-benzotriazol-2-yl)-4-(2,4,4-trimethylpentan-2-yl)phenol) (7.39 mmol, 5.0 g) was dissolved in ethanol (5 mL) along with scandium triflate (0.74 mmol, 364 mg) and hydrogen peroxide.urea adduct (8.5 mmol, 820 mg). The reaction stirred at 80° C. overnight and the white precipitate was filtered and washed with water and ethanol. A 2:1 mixture of the sulfoxide:sulfone was isolated (4.18 g, 81% yield).

Synthesis Example SE17: Phenol 23

6,6'-sulfonylbis(2-(2H-benzotriazol-2-yl)-4-(2,4,4-trimethylpentan-2-yl)phenol)

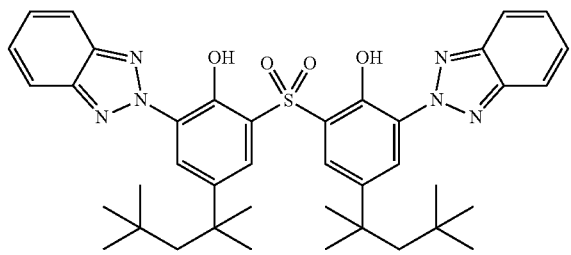 [SMILES: CC(C)(C)CC(C)(C)c1cc(-n2nc3ccccc3n2)c(O)c(S(=O)(=O)c2cc(C(C)(C)CC(C)(C)C)cc(-n3nc4ccccc4n3)c2O)c1]

6,6'-Sulfonylbis(2-(2H-benzotriazol-2-yl)-4-(2,4,4-trimethylpentan-2-yl)phenol) was synthesized in a similar fashion as Example 24. Aryl sulfide from SE10 (4.5 g, 6.6 mmol) was dissolved in dichloromethane (33 mL) in a flask equipped with a stir bar. m-Chloroperoxybenzoic acid, 50 wt % (7.40 mmol, 5.05 g) was added and the reaction stirred until complete by TLC. The reaction was then quenched with saturated aqueous NaHCO$_3$ and the organic layer separated, dried (Na$_2$SO$_4$), filtered, and concentrated. It was purified by washing with EtOAc and filtering. A white solid was obtained (2.9 g, 62% yield).

Synthesis Example SE18: Phenol 24

6,6'-(octadecylazanediyl)bis(2-(2H-benzotriazol-2-yl)-4-(2,4,4-trimethylpentan-2-yl)phenol)

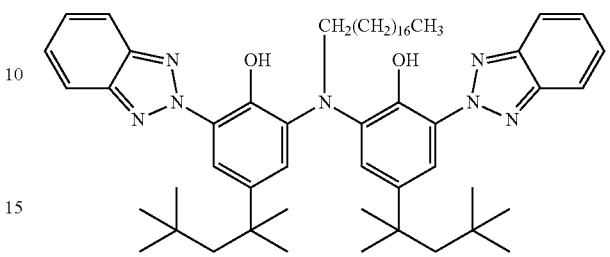

Part A. The reaction product from part A of SE8, (4.0 g, 5.81 mmol) was dissolved in dimethylformamide (60 mL) and to this, sodium hydride (6.40 mmol, 256 mg) was added under a stream of N$_2$ at rt. The mixture was stirred 10 min and then 1-iodooctadecane (6.40 mmol, 2.43 g) was added and stirring continued for another 2 h. The reaction was quenched with saturated aq ammonium chloride and extracted with EtOAc (3×). The combined organic layers were washed with water and then brine, dried with Na$_2$SO$_4$, filtered and concentrated. No further purification was performed.

Part B. The product of Part A was dissolved in dichloromethane (40 mL) and cooled to a temperature of −78° C. while stirring under N$_2$. Boron tribromide (12.20 mmol, 1.2 mL) was added dropwise and the reaction mixture allowed to slowly warm to rt. When the reaction was complete (analysis by TLC), water was added dropwise and the mixture was stirred for 10 min. The organic layer was separated and the aqueous layer extracted with DCM (2×). The combined organic layers were washed with saturated aqueous NaHCO$_3$ and brine, dried (Na$_2$SO$_4$ or MgSO$_4$), filtered and concentrated to give a viscous oil (5.16 g, 97% yield).

General Synthesis of Phenolate Salts

The above described phenols were used to prepare phenolate salts using one of the synthetic routes described below. The reagents used to prepare the salts are shown in Tables A and B and the phenolate salts formed are summarized in Table 1 below.

Synthetic Procedures

Alkoxide Route

Phenolic starting material is added to THF at 10-40% in a two-necked RBF equipped with a magnetic stir bar, condenser and addition funnel. The solution is stirred and heated to reflux until all of the phenolic starting material is dissolved under nitrogen. A stoichometric amount of metal alkoxide stock solution is added dropwise from the addition funnel to the RBF under nitrogen. The solution is refluxed from 1 to 36 hours. The solution is stripped with reduced pressure, and the recovered powder is dried in under vacuum.

Hydride Route

Anhydrous methanol is added to a dry, three-necked RBF equipped with a magnetic stir bar, reflux condenser, nitrogen inlet, and a stoppered port. The metal hydride is added to the RBF and refluxed under nitrogen for 30 minutes. The amount of hydride is used is added in 1-5% stoichiometric excess relative to the phenol being used, and the amount of phenol used is typically between 10-50% solids. After 30 minutes, the reaction is allowed to cool to room temperature and a stoichiometric amount of phenol is added the reaction by unstoppering the third port and adding the phenol in portions with a spatula. The reaction mixture is restoppered and stirred under nitrogen for 24 hours, at which point the reaction mixture is vacuum filtered and dried under vacuum. We have also prepared hypostoichometric compounds where less than the stoichometric amount of cation is used and hyperstoichometric amounts where a stoichometric excess amount of cation is used.

Metal Route

The metal in its zero oxidation state was stirred with an alcohol in one flask, while the phenol was stirred in an appropriate organic solvent in a separate flask. A typical solvent was toluene. The solutions are combined into one flask once the metal was fully digested by the alcohol. The resulting precipitate was vacuum filtered, washed with methanol, and dried under vacuum.

Alternative Routes

Other alternative routes can be envisioned for making these complexes. These routes could include reacting the phenols with an organometallic, such as butyl lithium.

Materials

The following is a table of commercially available materials and reagents that were used to prepare the phenolate salts

TABLE B

Listing of reagents used to prepare phenolate salts

| Material | Source | Supplied Form |
|---|---|---|
| $CaH_2$ | MP Biomedicals | Powder |
| $Mg(OCH_3)_2$ | Sigma-Aldrich | Powder |
| $Ca(OCH_3)_2$ | Sigma-Aldrich | Powder |
| $Li(OCH_3)$ | Sigma-Aldrich | 2.2M in methanol |
| $Na(OCH_2CH_3)$ | Alfa-Aesar | 21% w/v in ethanol |
| $K(OCH_3)$ | Sigma-Aldrich | 25% in methanol |
| Tetraethyl orthotitanate | TCI America | Liquid |
| Co(II) $(OCH_2CH_2OCH_3)_2$ | Alfa-Aesar | 5% w/v in methoxyethanol |
| Ca metal, granules | Alfa-Aesar | Granules |
| Methoxyethanol | Alfa-Aesar | Liquid |

TABLE C

Listing of phenols used in preparing phenolate salts

| Phenol | Trade Name | Source |
|---|---|---|
| Phenol-1 | TINUVIN P | BASF |
| Phenol-2 | — | Sigma-Aldrich |
| Phenol-3 | — | Synthesis Example SE3 |
| Phenol-4 | TINUVIN 327 | BASF |
| Phenol-5 | — | Synthesis Example SE2 |
| Phenol-6 | — | Synthesis Example SE3 |
| Phenol-7 | — | Synthesis Example SE4 |
| Phenol-8 | — | Synthesis Example SE5 |
| Phenol-9 | — | Synthesis Example SE6 |
| Phenol-10 | TINUVIN 234 | BASF |
| Phenol-11 | — | Synthesis Example SE7 |
| Phenol-12 | TINUVIN 360 | BASF |
| Phenol-13 | — | Synthesis Example SE8 |
| Phenol-14 | — | Synthesis Example SE9 |
| Phenol-15 | — | Synthesis Example SE10 |
| Phenol-16 | CGL 136 | CIBA |
| Phenol-17 | — | Synthesis Example SE11 |
| Phenol-18 | — | Synthesis Example SE12 |
| Phenol-19 | — | Synthesis Example SE13 |
| Phenol-20 | — | Synthesis Example SE14 |
| Phenol-21 | — | Synthesis Example SE15 |
| Phenol-22 | — | Synthesis Example SE16 |
| Phenol-23 | — | Synthesis Example SE17 |
| Phenol-24 | — | Synthesis Example SE18 |

TABLE 1

Metal Salts

| Material | Phenolate | Cation |
|---|---|---|
| Complex-1 | Phenol-1 | Na |
| Complex-2 | Phenol-1 | K |
| Complex-3 | Phenol-2 | Na |
| Complex-4 | Phenol-3 | K |
| Complex-5 | Phenol-4 | Na |
| Complex-6 | Phenol-5 | Na |
| Complex-7 | Phenol-6 | Na |
| Complex-8 | Phenol-7 | Na |
| Complex-9 | Phenol-8 | Na |
| Complex-10 | Phenol-9 | Na |
| Complex-11 | Phenol-10 | Na |
| Complex-12 | Phenol-10 | K |
| Complex-13 | Phenol-11 | Na |
| Complex-14 | Phenol-12 | Li |
| Complex-15 | Phenol-12 | Na |
| Complex-16 | Phenol-12 | Mg |
| Complex-17[a] | Phenol-12 | Ca |
| Complex-18[b] | Phenol-12 | Ca |
| Complex-19 | Phenol-12 | Co |
| Complex-20[c] | Phenol-12 | Ca |
| Complex 21 | Phenol-12 | K |
| Complex-22 | Phenol-13 | Ca |
| Complex-23 | Phenol-13 | Na |
| Complex-24 | Phenol-14 | Ca |
| Complex-25 | Phenol-14 | Na |
| Complex-26 | Phenol-15 | Ca |
| Complex-27 | Phenol-15 | Na |
| Complex-28 | Phenol-16 | Na |
| Complex-29 | Phenol-17 | Na |
| Complex-30 | Phenol-18 | Na |
| Complex-31 | Phenol-19 | Na |
| Complex-32 | Phenol-20 | Na |
| Complex-33 | Phenol-21 | Na |
| Complex-34 | Phenol-22 | Ca |
| Complex-35 | Phenol-22 | Na |
| Complex-36 | Phenol-23 | Ca |
| Complex-37 | Phenol-23 | Na |
| Complex-38[c] | Phenol-23 | Ca |
| Complex-39 | Phenol-24 | Ca |

[a]Synthesized by the hydride route;
[b]Synthesized by the alkoxide route;
[c]Synthesized by the metal route Computational Data As described above, an unexpected feature of these salt compounds is that they form multi-metal centered complexes comprised of one, two, three, or more phenolates. We refer to these compounds as macromolecular salt compositions. For simplicity, the macromolecular salt compositions are referred to as monomers, dimers, trimers, etc, using the standard macromolecular nomenclature. To demonstrate this feature, the heats of reaction, $\Delta H_{rxn}$, were computed for several model compounds using the following generalized reaction scheme:

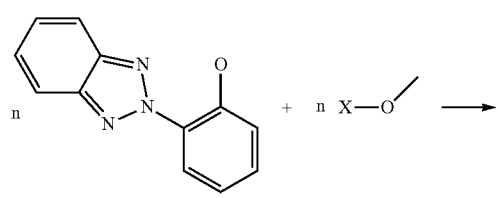 + n X—O⟶

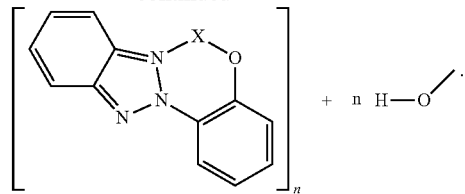 + n H—O

The heats of reaction were calculated by first optimizing the structures with the B3LYP density functional and MIDI! basis set followed by a frequency calculation to verify that the structure is a local minima. The geometry was further refined by optimizing with the B3LYP density functional and 6-31G(d,p) basis set. The heats of reaction are computed from the B3LYP/6-31G(d,p) electronic energies. The reported heats of reaction have been normalized to the number of metal centers. All computations were run with NWChem 6.5 (M. Valiev, E. J. Bylaska, N. Govind, K. Kowalski, T. P. Straatsma, H. J. J. van Dam, D. Wang, J. Nieplocha, E. Apra, T. L. Windus, W. A. de Jong, "NWChem: a comprehensive and scalable open-source solution for large scale molecular simulations" Comput. Phys. Commun. 181, 1477, 2010). The results are reported in Table 2.

TABLE 2

Computed heats of reactions in kcal/mol

| Model Compound | Metal | $\Delta H_{rxn}$ | | | |
|---|---|---|---|---|---|
| | | Monomer | Dimer | Trimer | Tetramer |
| (i-Pr substituted benzotriazole-phenol) | Na | 23.6 | 47.6 | 51.3 | 51.5 |
| | K | 23.1 | 43.2 | 48.5 | 47.4 |
| (n-C4 substituted benzotriazole-phenol) | Na | 24.3 | 46.8 | 52.5 | 49.7 |
| (n-C4, I substituted benzotriazole-phenol) | Na | 25.0 | 54.9 | 58.2 | 55.5 |

TABLE 2-continued

Computed heats of reactions in kcal/mol

| Model Compound | Metal | Monomer | Dimer | Trimer | Tetramer |
|---|---|---|---|---|---|
| 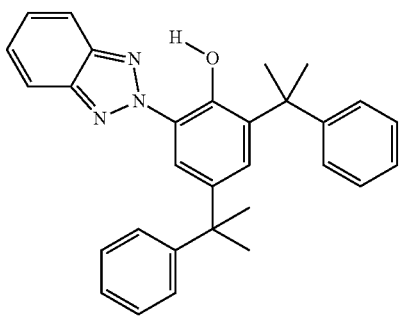 [SMILES: CC(C)(c1ccccc1)c1cc(-n2nc3ccccc3n2)c(O)c(C(C)(C)c2ccccc2)c1] | Na<br>K | 31.9<br>33.0 | 55.4<br>51.1 | 45.3<br>45.8 | |
| 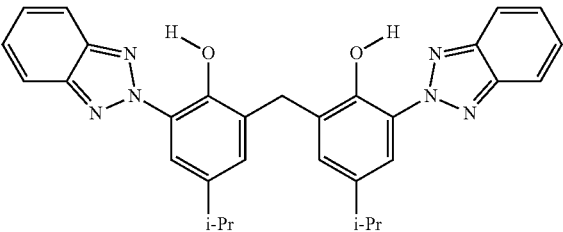 [SMILES: CC(C)c1cc(Cc2cc(C(C)C)cc(-n3nc4ccccc4n3)c2O)c(O)c(-n2nc3ccccc3n2)c1] | Na<br>Ca | 36.3<br>15.9 | 47.7<br>56.6 | 51.3<br>59.2 | |
| 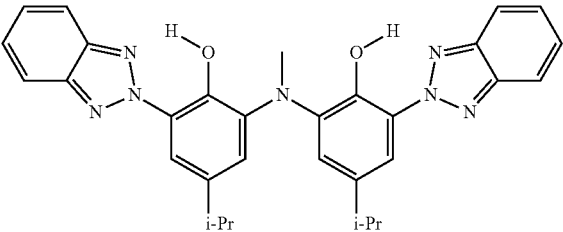 [SMILES: CC(C)c1cc(N(C)c2cc(C(C)C)cc(-n3nc4ccccc4n3)c2O)c(O)c(-n2nc3ccccc3n2)c1] | Ca | 19.0 | 53.1 | 56.7 | |

NMR Data

Sample Prep:

The deuterated solvents used in this study were tetrahydrofuran (THF) or benzene. The solvent was chosen based on the solubility of both the parent phenol and metal complex. Additionally, the solvents should not disrupt the bonding by replacing a ligand in the complex. The concentration of the prepared samples was kept low such that the solute concentration has a negligible effect on the viscosity of the deuterated solvent selected. If the viscosity of the deuterated solvent was low (most organic solvents), the sample was prepared in a 3 mm NMR tube rather than the 5 mm NMR tube to eliminate convection in the tube.

Measurement and Data Processing:

The Diffusion measurements were carried out on either the Bruker 500 MHz or Bruker 600 MHz NMR spectrometers. The gradients were suitably calibrated using a deuterated water sample. The standard Bruker 2D-DOSY sequence ledbpgp2s was used. For non-polymeric samples, the default settings of $\Delta=75$ ms and $\delta=3$ ms are sufficient. If the size of the complex or aggregate is expected to have a radius $>1$ nm, then increasing $\Delta$ may be necessary. For a description of the DOSY pulse sequence, refer to Antalek, B., *Concepts in Magnetic Resonance*, 14(4), 225-258 (2002).

The data was processed using Bruker Top Spin software. This is most suitable if there isn't spectral overlap between the compound of interest and residual monomer or another impurity in the sample. Selecting an exponential fit with a single component for each data point worked very well. The diffusion coefficient of the water or the main deuterated solvent can be used as internal controls from sample to sample to ensure there hasn't been a large viscosity change of the solution compared to the neat deuterated solvent. The diffusion coefficient of the analyte is measured in $m^2/s$.

The diffusion spectra of the starting material and the phenolate complex can be overlaid to easily visualize the difference in the diffusion coefficients.

The proton spectra for many of the complexes are quite different from the starting material. The first difference was the disappearance of the OH proton observed in the starting material at about 12 ppm.

Also observed in the proton spectra is a splitting of many of the resonances. For example the 2 t-butyl groups on the iso-C8 groups are a single resonance in the starting material with a peak at about 0.78 ppm. Upon reaction to form a metal complex, this resonance is often seen to split. In this example (Shown in the FIGURE) the resonance splits into 6 distinct narrow peaks. This is the result of different t-butyl groups on different molecules experience distinct magnetic environments. Exchange NMR experiments were carried out, but no chemical exchange among the multiple t-butyl resonances in complex was observed using NOESY experiments.

Aggregation numbers were calculated using an empirical relationship. The diffusion coefficients are plotted versus the molecular weight on a log-log plot. According to several references, there should be a linear relationship if the molecules have similar fractal exponents (Augé, S. et al.; *J. Phys. Chem. B*, 113, 1914-1918, (2009). Neufeld, R., Stalke, D.; *Chem. Sci.*, DOI: 10.1039/c5 sc00670h, (2015).).
The linear regression results in empirical formulas relating the Log of the molecular weight to the log of the diffusion coefficient in Benzene:

Log $M$=–(1/0.73825)*(Log $D$+6.99798)

And in THF:

Log $M$=–(1/0.66235)*(Log $D$+7.11205)

These relationships are used to estimate the molecular weight of the phenolate complexes formed. The results are reported in Table 3.

TABLE 3

Diffusion coefficients and estimated size of complex.

| Structure | Solvent | log D | estimated size |
|---|---|---|---|
| Phenol 1 | THF | −8.698 | 1 |
| Complex 1 | THF | −8.936 | 3 |
| Complex 2 | THF | −8.978 | 3 |
| Phenol 2 | THF | −8.743 | 1 |
| Complex 3 | THF | −8.916 | 2 |
| Phenol 3 | THF | −8.764 | 1 |
| Complex 4 | THF | −9.016 | 3 |
| Phenol 4 | THF | −8.847 | 1 |
| Complex 5 | THF | −8.913 | 2 |
| Phenol 5 | Benzene | −8.932 | 1 |
| Complex 6 | Benzene | −9.194 | 2 |
| Phenol 7 | THF | −8.88 | 1 |
| Complex 8 | THF | −9.14 | 3 |
| Phenol 8 | THF | −8.92 | 1 |
| Complex 9 | THF | −9.06 | 2 |
| Phenol 9 | THF | −8.80 | 1 |
| Complex 10 | THF | −9.18 | 2 |
| Phenol 10 | Benzene | −9.006 | 1 |
| Complex 11 | Benzene | −9.101 | 2 |
| Complex 12 | Benzene | −9.142 | 2 |
| Phenol 11 | THF | −8.948 | 1 |
| Complex 13 | THF | −9.075 | 2 |
| Phenol 12 | Benzene | −9.098 | 1 |
| Complex 14 | Benzene | −9.371 | 3 |
| Complex 15 | Benzene | −9.293 | 2 |
| Complex 17 | Benzene | −9.390 | 3 |
| Complex 18 | Benzene | −9.389 | 3 |
| Complex 19 | Benzene | −9.425 | 3 |
| Phenol 13 | Benzene | −9.087 | 1 |
| Complex 23 | Benzene | −9.278 | 2 |
| Complex 22 | Benzene | −9.476 | 3 |
| Phenol 14 | Benzene | −9.103 | 1 |
| Complex 25 | Benzene | −9.297 | 2 |
| Phenol 15 | Benzene | −9.099 | 1 |
| Complex 26 | Benzene | −9.357 | 2 |
| Complex 27 | Benzene | −9.269 | 2 |
| Phenol 19 | THF | −8.880 | 1 |
| Complex 31 | THF | −9.019 | 2 |
| Phenol 20 | THF | −8.898 | 1 |
| Complex 32 | THF | −9.052 | 2 |
| Phenol 21 | THF | −8.911 | 1 |
| Complex 33 | THF | −9.059 | 2 |
| Phenol 22 | Benzene | −9.098 | 1 |
| Complex 34 | Benzene | −9.340 | 2 |
| Complex 35 | Benzene | −9.378 | 2 |
| Phenol 23 | Benzene | −9.106 | 1 |
| Complex 37 | Benzene | −9.288 | 2 |
| Complex 38 | Benzene | −9.329 | 2 |
| Complex 39 | Benzene | −9.319 | 2 |
| Phenol 24 | Benzene | −9.180 | 1 |
| Complex 39 | Benzene | −9.367 | 2 |

Thermal Stability of Metal-Complexes

The thermal stability of the phenols and phenolates was measured by thermogravemetric analysis (TGA). The instrument used was the Q500 model made by TA Instruments. The procedure was to heat a dried sample at 10° C./min under Nitrogen to a temperature of 450° C. The starting temperature was around 35° C. and a typical sample size was 5 mg. The temperatures for 5%, 10%, and 20% weight loss are reported in Table 4. In some cases it was necessary to drive off absorbed solvent or water in order to report accurate weight losses. This was achieved by heating the sample to a temperature no greater than 180° C., cooling the sample back to room temperature, and then reheating to a temperature of 450° C.

TABLE 4

Temperatures in Celsius for 5, 10, and 20 percent weight loss as measured by TGA.

| Molecule | 5% Weight Loss | 10% Weight Loss | 20% Weight Loss |
|---|---|---|---|
| Phenol-1 | 180 | 195 | 211 |
| Complex 1 | 285 | 288 | 308 |
| Complex 2 | 340 | 377 | 425 |
| Phenol 2 | 195 | 209 | 226 |
| Complex 3 | 251 | 257 | 282 |
| Phenol 3 | 95 | 195 | 212 |
| Complex 4 | 240 | 251 | 269 |
| Phenol 4 | 208 | 222 | 238 |
| Complex 5 | 386 | 403 | 442 |
| Phenol 5 | 230 | 249 | 269 |
| Complex 6 | 376 | 387 | 397 |
| Phenol 7 | 231 | 247 | 264 |
| Complex 8 | 337 | 345 | 354 |
| Phenol 8 | 250 | 270 | 289 |
| Complex 9 | 268 | 297 | 336 |
| Phenol 9 | 264 | 283 | 302 |
| Complex 10 | 418 | 431 | 444 |
| Phenol 10 | 264 | 280 | 295 |
| Complex 12 | 258 | 290 | 328 |
| Phenol 11 | 304 | 323 | 343 |
| Complex 13 | 319 | 350 | 394 |
| Phenol 12 | 335 | 352 | 371 |
| Complex 14 | 341 | 377 | 425 |
| Complex 15 | 321 | 360 | 414 |
| Complex 17 | 325 | 359 | 399 |
| Complex 19 | 257 | 300 | 322 |
| Complex 20 | 413 | 444 | 465 |
| Phenol 13 | 348 | 373 | 394 |
| Complex 22 | 384 | 407 | 432 |
| Complex 23 | 417 | 426 | 436 |
| Phenol 14 | 321 | 350 | 377 |
| Complex 24 | 333 | 371 | 403 |
| Complex 25 | 384 | 412 | 428 |
| Phenol 15 | 243 | 291 | 353 |
| Complex 26 | 414 | 424 | 441 |
| Complex 27 | 381 | 394 | 400 |
| Phenol 16 | 260 | 275 | 293 |
| Complex 28 | 265 | 283 | 299 |
| Phenol 17 | 247 | 261 | 278 |
| Complex 29 | 334 | 346 | 356 |
| Phenol 18 | 256 | 275 | 295 |
| Complex 30 | 267 | 304 | 331 |
| Phenol 19 | 271 | 289 | 308 |
| Complex 31 | 357 | 375 | 386 |
| Phenol 20 | 183 | 256 | 267 |
| Complex 32 | 389 | 389 | 390 |
| Phenol 21 | 264 | 305 | 329 |
| Complex 33 | 400 | 406 | 408 |
| Phenol 22 | 242 | 263 | 294 |
| Complex 34 | 387 | 409 | 440 |
| Complex 35 | 361 | 370 | 409 |
| Phenol 23 | 210 | 330 | 361 |
| Complex 36 | 356 | 394 | 421 |
| Complex 37 | 211 | 359 | 385 |
| Complex 38 | 359 | 386 | 416 |

TABLE 4-continued

Temperatures in Celsius for 5, 10, and 20
percent weight loss as measured by TGA.

| Molecule | 5% Weight Loss | 10% Weight Loss | 20% Weight Loss |
|---|---|---|---|
| Phenol 24 | 296 | 343 | 365 |
| Complex 39 | 277 | 321 | 354 |

Fluorescence Observations

Step A: Preparation of Samples

A spatula-tip of either phenol or metal complex was added with 2 mL of THF to a clean vial. The vial was sealed and the vial sat until the chemical completely dissolved.

Step B: Fluorescence Determination

The vials were and exposed to 365 nm wavelength UV light source in a darkened room and visual observations were recorded. The data are shown in Table 5 below.

TABLE 5

Fluorescence observations.

| Molecule | Fluorescent |
|---|---|
| Phenol 1 | No |
| Complex 1 | Strong |
| Complex 2 | Moderate-Strong |
| Phenol 2 | Weak |
| Complex 3 | Moderate-Strong |
| Phenol 4 | No |
| Complex 5 | Moderate (red) |
| Phenol 5 | No |
| Complex 6 | Strong |
| Phenol 7 | No |
| Complex 8 | Moderate-Strong |
| Phenol 8 | Weak |
| Complex 9 | Moderate-Strong |
| Phenol 9 | No |
| Complex 10 | Strong |
| Phenol 10 | No |
| Complex 11 | Moderate-Strong |
| Complex 12 | Moderate-Strong |
| Phenol 11 | Weak |
| Complex 13 | Moderate-Strong |
| Phenol 12 | No |
| Complex 14 | Strong |
| Complex 15 | Moderate-Strong |
| Complex 16 | Strong |
| Complex 17 | Moderate-Strong |
| Complex 18 | Moderate-Strong |
| Phenol 14 | No |
| Complex 24 | Moderate-Strong |
| Complex 25 | Moderate-Strong (orange) |
| Phenol 15 | No |
| Complex 26 | Strong (green) |
| Complex 27 | Strong |
| Phenol 16 | No |
| Complex 28 | No |
| Phenol 17 | No |
| Complex 29 | Weak |
| Complex 30 | No |
| Phenol 19 | No |
| Complex 31 | Moderate-Strong (orange) |
| Phenol 20 | No |
| Complex 32 | Strong (green) |
| Phenol 21 | Weak |
| Complex 33 | Strong (green) |
| Phenol 22 | No |
| Complex 34 | Strong (green) |
| Complex 35 | Strong |
| Phenol 23 | No |
| Complex 36 | Strong (blue) |
| Complex 37 | Strong (blue) |
| Complex 38 | Strong |
| Phenol 24 | No |
| Complex 39 | Moderate-Strong (orange) |

Anti-Oxidant Studies

Step A—Preparation of Compounded Additives

To prepare the samples, one of the additives was dry blended into polypropylene.

The concentration is specified in Table 6 below. The materials were compounded in a conical twin-screw extruder. The extrusion temperature ranged from about 250° C. to 300° C. The extrusion speeds ranged from 5 to 7 lbs/hr. The resins used were either MF-650X (PP-1) or MF-650W (PP-2), where both resins were purchased from Lyondell-Basell.

Step B—Determination of Anti-Oxidant Ability

A modified oxidative-induction time (OIT) test that is similar to ASTM D3895 was performed. In the modified test, 2-6 mg of sample were placed in an aluminum pan and heated to 190° C. under nitrogen in a differential scanning calorimeter (DSC). The atmosphere was then switched to an atmosphere of 21% oxygen and 78% nitrogen and the temperature at between was held at 180° C. and 200° C. until an abrupt increase in evolved heat was displayed on the recorded thermogram. The induction time was then defined as the time between exposure to the oxygen-containing environment and onset of heat evolution. The data presented in Table 6 are an average of 3 samples.

TABLE 6

OIT data for metal complexes.

| Resin | Additive | Additive Concentration | Temperature (° C.) | OIT (min) |
|---|---|---|---|---|
| PP-1 | | | 180 | 45.0 |
| PP-2 | | | 180 | 26.5 |
| PP-1 | | | 190 | 18.1 |
| PP-1 | | | 200 | 6.5 |
| PP-1 | Phenol 11 | 0.2% | 200 | 291.1 |
| PP-1 | Complex 13 | 0.2% | 200 | 342.7 |
| PP-1 | Complex 9 | | 190 | 32.8 |
| PP-2 | Phenol 12 | 0.2% | 180 | 27.7 |
| PP-1 | Complex 21 | | 180 | 53.4 |
| PP-2 | Complex 17 | | 180 | 81.6 |
| PP-2 | Complex 17 | | 180 | 107.7 |
| PP-1 | Complex 24 | 0.6% | 190 | 151.2 |
| PP-1 | Phenol 13 | 0.2% | 190 | 29.9 |
| PP-1 | Complex 22 | 0.2% | 190 | 187.6 |
| PP-1 | Phenol 14 | 0.2% | 190 | 5.05 |
| PP-1 | Complex 24 | 0.2% | 190 | 62.7 |

What is claimed is:

1. An antioxidant composition comprising one or more macromolecular salt compositions, the macromolecular salt composition comprising an assembly of metal salts comprising repeat units of the structure:

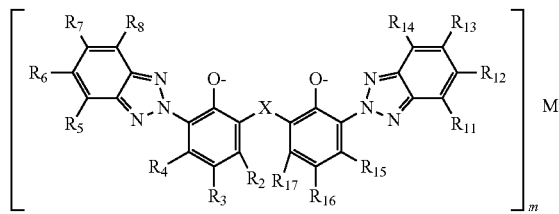
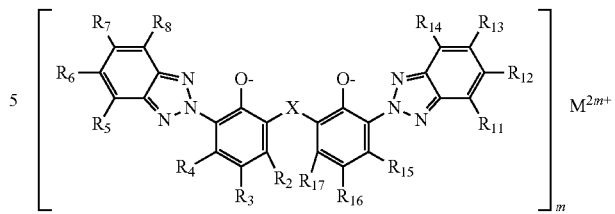

wherein X comprises a —O—, —S—, —S(O)$_2$—, or —NR$^{10}$—linking group where R$^{10}$ comprises a hydrogen atom, an alkyl group, or an aryl group;

each R$^2$, R$^3$, R$^4$, R$^5$, R$^6$, R$^7$, R$^8$, R$^{11}$, R$^{12}$, R$^{13}$, R$^{14}$, R$^{15}$, R$^{16}$, and R$^{17}$, independently comprises a hydrogen atom, an alkyl group, an alkenyl group, an aryl group, or a halogen atom;

m=0.5, 1, or 2;

M is a metal ion with a valency of 2m such that M is lithium sodium or potassium when m=0.5;

M is calcium, magnesium, or cobalt, when m=1; and M is vanadium or titanium when m=2.

2. The antioxidant composition of claim 1, wherein X comprises a —NR$^{10}$—linking group, where R$^{10}$ comprises a hydrogen atom or an alkyl group comprising 1-3 carbon atoms, and R$^3$ and R$^{16}$ each comprises an alkyl group with 1-20 carbon atoms.

3. The antioxidant composition of claim 1, wherein X comprises a —NR$^{10}$—linking group, where R$^{10}$ comprises a hydrogen atom, and R$^3$ and R$^{16}$ each comprises an alkyl group with 8 carbon atoms.

4. The antioxidant composition of claim 1, wherein X comprises a —NR$^{10}$—linking group, where R$^{10}$ comprises a methyl group, and R$^3$ and R$^{16}$ each comprises an alkyl group with 8 carbon atoms.

5. The antioxidant composition of claim 1, wherein X comprises a —S—linking group, and R$^3$ and R$^{16}$ each comprises an alkyl group with 1-20 carbon atoms.

6. The antioxidant composition of claim 1, wherein X comprises a —S—linking group, and R$^3$ and R$^{16}$ each comprises an alkyl group with 8 carbon atoms.

7. The antioxidant composition of claim 1, wherein X comprises a —O—linking group, and R$^3$ and R$^{16}$ each comprises an alkyl group with 1-20 carbon atoms.

8. The antioxidant composition of claim 1, wherein X comprises a —O—linking group, and R$^3$ and R$^{16}$ each comprises an alkyl group with 8 carbon atoms.

9. A macromolecular salt composition comprising an assembly of metal salts comprising repeat units of a substituted benzotriazole phenolate anion and a metal cation with the structure:

wherein X comprises a —O—, —S—, —S(O)—, —S(O)$_2$—, or —NR$^{10}$—linking group where R'$^{o}$ comprises a hydrogen atom, an alkyl group, or an aryl group;

each R$^2$, R$^3$, R$^4$, R$^5$, R$^6$, R$^7$, R$^8$, R$^{11}$, R$^{12}$, R$^{13}$, R$^{14}$, R$^{15}$, R$^{16}$, and R$^{17}$, independently comprises a hydrogen atom, an alkyl group, an alkenyl group, an aryl group, or a halogen atom;

m=0.5, 1, or 2;

M is a metal ion with a valency of 2m such that M is lithium sodium or potassium when m=0.5;

M is calcium, magnesium, or cobalt, when m=1; and M is vanadium or titanium when m=2.

10. The salt composition of claim 9, wherein X comprises a —NR$^{10}$—linking group, where R$^{10}$ comprises a hydrogen atom or an alkyl group comprising 1-3 carbon atoms, and R$^3$ and R$^{16}$ each comprises an alkyl group with 1-20 carbon atoms.

11. The salt composition of claim 9, wherein X comprises a —NR$^{10}$—linking group, where R$^{10}$ comprises a hydrogen atom, and R$^3$ and R$^{16}$ each comprises an alkyl group with 8 carbon atoms.

12. The salt composition of claim 9, wherein X comprises a —NR$^{10}$—linking group, where R$^{10}$ comprises a methyl group, and R$^3$ and R$^{16}$ each comprises an alkyl group with 8 carbon atoms.

13. The salt composition of claim 9, wherein X comprises a —S—linking group, and R$^3$ and R$^{16}$ each comprises an alkyl group with 1-20 carbon atoms.

14. The salt composition of claim 9, wherein X comprises a —S—linking group, and R$^3$ and R$^{16}$ each comprises an alkyl group with 8 carbon atoms.

15. The salt composition of claim 9, wherein X comprises a —O—linking group, and R$^3$ and R$^{16}$ each comprises an alkyl group with 1-20 carbon atoms.

16. The salt composition of claim 9, wherein X comprises a —O—linking group, and R$^3$ and R$^{16}$ each comprises an alkyl group with 8 carbon atoms.

\* \* \* \* \*